United States Patent
Li

(10) Patent No.: US 9,314,210 B2
(45) Date of Patent: Apr. 19, 2016

(54) METHOD AND APPARATUS FOR RATE-DEPENDENT MORPHOLOGY-BASED CARDIAC ARRHYTHMIA CLASSIFICATION

(75) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1446 days.

(21) Appl. No.: 11/151,567

(22) Filed: Jun. 13, 2005

(65) Prior Publication Data

US 2006/0281998 A1 Dec. 14, 2006

(51) Int. Cl.
| | | |
|---|---|---|
| A61B 5/04 | (2006.01) | |
| A61B 5/00 | (2006.01) | |
| A61B 5/0452 | (2006.01) | |
| A61B 5/0464 | (2006.01) | |

(52) U.S. Cl.
CPC ............ *A61B 5/7264* (2013.01); *A61B 5/0464* (2013.01); *A61B 5/04525* (2013.01)

(58) Field of Classification Search
CPC . A61B 5/04525; A61B 5/0464; A61B 5/7264
USPC .................................................. 600/515–518
See application file for complete search history.

(56) References Cited

U.S. PATENT DOCUMENTS

| | | |
|---|---|---|
| 4,023,564 A | 5/1977 | Valiquette et al. |
| 4,336,810 A | 6/1982 | Anderson et al. |
| 4,531,527 A | 7/1985 | Reinhold, Jr. et al. |
| 4,583,553 A | 4/1986 | Shah et al. |
| 4,589,420 A | 5/1986 | Adams et al. |
| 4,721,114 A | 1/1988 | DuFault et al. |

(Continued)

FOREIGN PATENT DOCUMENTS

| | | |
|---|---|---|
| DE | 4405827 | 6/1995 |
| EP | 0469817 | 2/1992 |

(Continued)

OTHER PUBLICATIONS

Duru, Firat, et al., "The Potential for Inappropriate Ventricular Tachycardia Confirmation Using the Intracardiac Electrogram (EGM) Width Criterion", *PACE*, vol. 22, 1999, (Jul. 1999), 1039-1046.

(Continued)

*Primary Examiner* — Niketa Patel
*Assistant Examiner* — Lindsey G Hankins
(74) *Attorney, Agent, or Firm* — Schwegman Lundberg & Woessner, P.A.

(57) ABSTRACT

An implantable medical device includes a tachyarrhythmia detection and classification system that classifies tachyarrhythmias based on a morphological analysis of template and arrhythmic waveforms. The morphological analysis takes effect of heart rate on the morphological characteristics of the template and arrhythmic waveforms into consideration. Correlation between morphological features of the template waveform and corresponding morphological features of an arrhythmic waveform provides for the basis for classifying the tachyarrhythmia. In one embodiment, corresponding morphological features are extracted from the template and arrhythmic waveforms at locations determined by the heart rate associated with a detected arrhythmia episode. In another embodiment, weighting factors each being a function of the heart rate are applied to the template and arrhythmic morphological features before a correlation coefficient is calculated.

34 Claims, 12 Drawing Sheets

(56) References Cited

U.S. PATENT DOCUMENTS

| | | | |
|---|---|---|---|
| 4,802,491 A | 2/1989 | Cohen et al. | |
| 4,838,278 A | 6/1989 | Wang et al. | |
| 4,884,345 A | 12/1989 | Long | |
| 4,924,875 A | 5/1990 | Chamoun | |
| 4,947,857 A | 8/1990 | Albert et al. | |
| 5,000,189 A | 3/1991 | Throne et al. | |
| 5,014,284 A | 5/1991 | Langer et al. | |
| 5,014,698 A | 5/1991 | Cohen | |
| 5,020,540 A | 6/1991 | Cahmoun | |
| 5,092,341 A * | 3/1992 | Kelen | 600/515 |
| 5,107,850 A | 4/1992 | Olive | |
| 5,109,842 A | 5/1992 | Adinolfi | |
| 5,139,028 A | 8/1992 | Steinhaus et al. | |
| 5,156,148 A | 10/1992 | Cohen | |
| 5,184,615 A | 2/1993 | Nappholz et al. | |
| 5,193,550 A | 3/1993 | Duffin | |
| 5,215,098 A | 6/1993 | Steinhaus et al. | |
| 5,217,021 A | 6/1993 | Steinhaus et al. | |
| 5,240,009 A | 8/1993 | Williams | |
| 5,247,021 A | 9/1993 | Fujisawa et al. | |
| 5,255,186 A | 10/1993 | Steinhaus et al. | |
| 5,269,301 A | 12/1993 | Cohen | |
| 5,271,411 A | 12/1993 | Ripley et al. | |
| 5,273,049 A | 12/1993 | Steinhaus et al. | |
| 5,275,621 A | 1/1994 | Mehra | |
| 5,277,190 A | 1/1994 | Moulton | |
| 5,280,792 A | 1/1994 | Leong et al. | |
| 5,292,348 A | 3/1994 | Saumarez et al. | |
| 5,311,874 A | 5/1994 | Baumann et al. | |
| 5,312,445 A | 5/1994 | Nappholz et al. | |
| 5,313,953 A | 5/1994 | Yomtov et al. | |
| 5,330,504 A | 7/1994 | Somerville et al. | |
| 5,331,966 A | 7/1994 | Bennett et al. | |
| 5,350,406 A | 9/1994 | Nitzsche et al. | |
| 5,360,436 A | 11/1994 | Alt et al. | |
| 5,366,487 A | 11/1994 | Adams et al. | |
| 5,388,578 A | 2/1995 | Yomtov et al. | |
| 5,400,795 A | 3/1995 | Murphy et al. | |
| 5,404,880 A | 4/1995 | Throne | |
| 5,411,031 A | 5/1995 | Yomtov | |
| 5,421,830 A | 6/1995 | Epstein et al. | |
| 5,447,519 A | 9/1995 | Peterson | |
| 5,447,524 A | 9/1995 | Alt | |
| 5,456,261 A | 10/1995 | Luczyk | |
| 5,458,623 A | 10/1995 | Lu et al. | |
| 5,478,807 A | 12/1995 | Cronin et al. | |
| 5,503,159 A | 4/1996 | Burton | |
| 5,509,927 A | 4/1996 | Epstein et al. | |
| 5,520,191 A | 5/1996 | Karlsson et al. | |
| 5,542,430 A | 8/1996 | Farrugia et al. | |
| 5,609,158 A | 3/1997 | Chan | |
| 5,622,178 A | 4/1997 | Gilham | |
| 5,628,326 A | 5/1997 | Arand et al. | |
| 5,634,468 A | 6/1997 | Platt et al. | |
| 5,645,070 A | 7/1997 | Turcott | |
| 5,676,687 A | 10/1997 | Ayers | |
| 5,682,900 A | 11/1997 | Arand et al. | |
| 5,683,425 A | 11/1997 | Hauptmann | |
| 5,687,737 A | 11/1997 | Branham et al. | |
| 5,704,365 A | 1/1998 | Albrecht et al. | |
| 5,712,801 A | 1/1998 | Turcott | |
| 5,713,367 A | 2/1998 | Arnold et al. | |
| 5,724,985 A | 3/1998 | Snell et al. | |
| 5,730,142 A | 3/1998 | Sun et al. | |
| 5,738,105 A | 4/1998 | Kroll | |
| 5,755,739 A | 5/1998 | Sun et al. | |
| 5,759,158 A | 6/1998 | Swanson | |
| 5,772,604 A | 6/1998 | Langberg et al. | |
| 5,778,881 A | 7/1998 | Sun et al. | |
| 5,779,645 A | 7/1998 | Olson et al. | |
| 5,782,888 A | 7/1998 | Sun et al. | |
| 5,792,065 A | 8/1998 | Xue et al. | |
| 5,795,303 A | 8/1998 | Swanson et al. | |
| 5,797,399 A | 8/1998 | Morris et al. | |
| 5,797,849 A | 8/1998 | Vesely et al. | |
| 5,817,133 A | 10/1998 | Houben | |
| 5,819,007 A | 10/1998 | Elghazzawi | |
| 5,819,741 A | 10/1998 | Karlsson et al. | |
| 5,827,197 A | 10/1998 | Bocek et al. | |
| 5,848,972 A | 12/1998 | Triedman et al. | |
| 5,857,977 A | 1/1999 | Caswell et al. | |
| 5,858,977 A | 1/1999 | Aukerman et al. | |
| 5,868,680 A | 2/1999 | Steiner et al. | |
| 5,935,082 A | 8/1999 | Albrecht et al. | |
| 5,954,661 A | 9/1999 | Greenspon et al. | |
| 6,016,442 A | 1/2000 | Hsu et al. | |
| 6,192,273 B1 * | 2/2001 | Igel et al. | 607/14 |
| 6,223,078 B1 * | 4/2001 | Marcovecchio | 607/5 |
| 6,266,554 B1 | 7/2001 | Hsu et al. | |
| 6,275,732 B1 | 8/2001 | Hsu et al. | |
| 6,434,417 B1 | 8/2002 | Lovett | |
| 6,449,503 B1 * | 9/2002 | Hsu | 600/518 |
| 6,456,871 B1 | 9/2002 | Hsu et al. | |
| 6,480,734 B1 * | 11/2002 | Zhang et al. | 600/518 |
| 6,484,055 B1 | 11/2002 | Marcovecchio | |
| 6,493,579 B1 | 12/2002 | Gilkerson et al. | |
| 6,512,940 B1 | 1/2003 | Brabec et al. | |
| 6,522,917 B1 | 2/2003 | Hsu et al. | |
| 6,526,313 B2 | 2/2003 | Sweeney et al. | |
| 6,687,540 B2 | 2/2004 | Marcovecchio | |
| 6,708,058 B2 | 3/2004 | Kim et al. | |
| 6,728,572 B2 * | 4/2004 | Hsu et al. | 600/516 |
| 6,745,068 B2 | 6/2004 | Koyrakh et al. | |
| 6,760,615 B2 | 7/2004 | Ferek-Petric | |
| 6,766,190 B2 | 7/2004 | Ferek-Petric | |
| 6,889,081 B2 | 5/2005 | Hsu | |
| 6,959,212 B2 | 10/2005 | Hsu et al. | |
| 6,978,177 B1 | 12/2005 | Chen et al. | |
| 6,996,434 B2 | 2/2006 | Marcovecchio et al. | |
| 7,031,764 B2 | 4/2006 | Schwartz et al. | |
| 7,039,463 B2 | 5/2006 | Marcovecchio | |
| 7,184,818 B2 | 2/2007 | Kim et al. | |
| 2002/0032469 A1 | 3/2002 | Marcovecchio | |
| 2002/0049474 A1 | 4/2002 | Marcovecchio et al. | |
| 2002/0087091 A1 | 7/2002 | Koyrakh et al. | |
| 2002/0091333 A1 * | 7/2002 | Hsu et al. | 600/518 |
| 2002/0183637 A1 | 12/2002 | Kim et al. | |
| 2002/0183639 A1 | 12/2002 | Sweeney et al. | |
| 2002/0198461 A1 | 12/2002 | Hsu et al. | |
| 2003/0060849 A1 | 3/2003 | Hsu | |
| 2003/0074026 A1 | 4/2003 | Thompson et al. | |
| 2003/0083586 A1 | 5/2003 | Ferek-Petric | |
| 2003/0083587 A1 | 5/2003 | Ferek-Petric | |
| 2003/0100923 A1 | 5/2003 | Bjorling et al. | |
| 2003/0109792 A1 | 6/2003 | Hsu et al. | |
| 2003/0120316 A1 | 6/2003 | Spinelli et al. | |
| 2003/0181818 A1 | 9/2003 | Kim et al. | |
| 2004/0015090 A1 | 1/2004 | Sweeney et al. | |
| 2004/0093035 A1 | 5/2004 | Schwartz et al. | |
| 2004/0116972 A1 | 6/2004 | Marcovecchio | |
| 2004/0127806 A1 | 7/2004 | Sweeney | |
| 2004/0176694 A1 | 9/2004 | Kim et al. | |
| 2005/0010257 A1 | 1/2005 | Lincoln et al. | |
| 2005/0015978 A1 | 1/2005 | Andersen et al. | |
| 2005/0256544 A1 | 11/2005 | Thompson | |
| 2006/0074331 A1 * | 4/2006 | Kim et al. | 600/515 |
| 2006/0079796 A1 | 4/2006 | Marcovecchio et al. | |
| 2006/0095083 A1 | 5/2006 | Zhang et al. | |
| 2006/0122527 A1 | 6/2006 | Marcovecchio | |

FOREIGN PATENT DOCUMENTS

| | | |
|---|---|---|
| EP | 0506230 | 9/1992 |
| EP | 0554208 | 8/1993 |
| EP | 0711531 | 5/1996 |
| EP | 0776630 | 11/1996 |
| EP | 0776631 | 11/1996 |
| EP | 0848965 | 6/1998 |
| WO | WO-97/39681 | 4/1996 |
| WO | WO-97/11745 | 4/1997 |
| WO | WO-98/40010 | 9/1998 |

(56) References Cited

FOREIGN PATENT DOCUMENTS

| WO | WO-98/53879 | 12/1998 |
|---|---|---|
| WO | WO-0126733 A1 | 4/2001 |

OTHER PUBLICATIONS

Grady, Thomas A., et al., "Prognostice Significance of Exercise-Induced Left Bundle-Branch Block", *JAMA*, vol. 279, No. 2, Jan. 14, 1998, 153-156.

Hsu, William, "System and Method for Classifying Tachycardia Arrhythmias Having 1:1 Atrial to Ventricual Rhythms", U.S. Appl. No. 09/417,588, filed Oct. 13, 1999, 39 pgs.

Kinoshita, Shinji, et al., "Transient Disapperance of Complete Right Bundle Branch (BBB) During Exercise", *Journal of Electrocardiology*, vol. 29, No. 3, 1996, 255-256.

Li, Dan, "Methods and Apparatuses for Cardiac Arrhythmia Classification Using Morphology Stability", U.S. Appl. No. 11/038,996, filed Jan. 20, 2005, 74 pgs.

Ng, S. S., "Microcomputer-Based Telemetry System for ECG Monitoring", *IEEE Proc. of the Ann. Int'l Conf. of the Engineering in Medicine and Biology Society*, vol. Conf. 9, XP000015425, (1987), 1492-193.

Schwartz, Mark, et al., "Cardiac Rhythm Management Systems and Methods Using Multiple Morphology Templates for Discriminating Between Rhythms", U.S. Appl. No. 11/277,095, Date Mailed Mar. 21, 2006, 35 Pages.

Cazares, Shelley, et al., "Arrhythima Discrimination Based on Determination of Rate Dependency", U.S. Appl. No. 11/312,280, filed Dec. 20, 2005, 41 Pages.

Morris, Milton M., "Detection of Atrial Arrhythmia for Cardiac Rhythm Management by Implantable Devices", *Journal of Electrocardiology*, vol. 33, (2000), 133-139.

\* cited by examiner

METHOD AND APPARATUS FOR RATE-DEPENDENT MORPHOLOGY-BASED CARDIAC ARRHYTHMIA CLASSIFICATION

CROSS-REFERENCE TO RELATED APPLICATIONS

This application is related to co-pending, commonly assigned U.S. patent application Ser. No. 11/038,996, entitled "METHODS AND APPARATUSES FOR CARDIAC ARRHYTHMIA CLASSIFICATION," filed on Jan. 20, 2005, U.S. patent application Ser. No. 10/731,223, entitled "DISCRIMINATION OF SUPRAVENTRICULAR TACHYCARDIA AND VENTRICULAR TACHYCARDIA EVENTS," filed on Dec. 9, 2003, now U.S. Pat. No. 7,039,463, U.S. patent application Ser. No. 10/291,200, entitled "CARDIAC RHYTHM MANAGEMENT SYSTEMS AND METHODS USING MULTIPLE MORPHOLOGY TEMPLATES FOR DISCRIMINATING BETWEEN RHYTHMS," filed on Nov. 8, 2002, now U.S. Pat. No. 7,031,764, U.S. patent application Ser. No. 10/014,933, entitled "SYSTEM AND METHOD FOR ARRHYTHMIA DISCRIMINATION," filed on Oct. 22, 2001, now U.S. Pat. No. 6,959,212, and U.S. patent application Ser. No. 09/921,348, entitled "METHOD AND SYSTEM FOR VERIFYING THE INTEGRITY OF NORMAL SINUS RHYTHM TEMPLATES," filed Aug. 2, 2001, now U.S. pat. No. 6,996,434, which are hereby incorporated by reference in their entirety.

TECHNICAL FIELD

This document relates generally to cardiac rhythm management (CRM) systems and particularly, but not by way of limitation, to such a system providing for rate-dependent morphology-based classification of tachyarrhythmias.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract. The electrical conduction system includes, in the order by which the electrical impulses travel in a normal heart, internodal pathways between the SA node and the atrioventricular (AV) node, the AV node, the His bundle, and the Purkinje system including the right bundle branch (RBB, which conducts the electrical impulses to the RV) and the left bundle branch (LBB, which conducts the electrical impulses to the LV). More generally, the electrical impulses travel through an AV conduction pathway to cause the atria, and then the ventricles, to contract.

Tachyarrhythmia (also referred to as tachycardia) occurs when the heart contracts at a rate higher than a normal heart rate. Tachyarrhythmia generally includes ventricular tachyarrhythmia (VT) and supraventricular 0tachyarrhythmia (SVT). VT occurs, for example, when a pathological conduction loop formed in the ventricles through which electrical impulses travel circularly within the ventricles, or when a pathologically formed electrical focus generates electrical impulses from the ventricles. SVT includes physiologic sinus tachyarrhythmia and pathologic SVTs. The physiologic sinus tachyarrhythmia occurs when the SA node generates the electrical impulses at a particularly high rate. A pathologic SVT occurs, for example, when a pathologic conduction loop forms in an atrium. Fibrillation occurs when the heart contracts at a tachyarrhythmia rate with an irregular rhythm. Ventricular fibrillation (VF), as a ventricular arrhythmia with an irregular conduction, is a life threatening condition requiring immediate medical treatment such as ventricular defibrillation. Atrial fibrillation (AF), as a SVT with an irregular rhythm, though not directly life threatening, also needs medical treatment such as atrial defibrillation to restore a normal cardiac function and to prevent the deterioration of the heart.

Implantable medical devices such as implantable cardioverter/defibrillators (ICDs) are used to treat tachyarrhythmias, including fibrillation. To deliver an effective cardioversion/defibrillation therapy, the cardioversion/defibrillation energy is to be delivered to the chambers of the heart where the tachyarrhythmia or fibrillation originates. When the atrial rate of depolarizations (or contractions) is substantially different from the ventricular rate of depolarizations (or contractions), the atrial and ventricular rates of depolarizations (or contractions) provide for a basis for locating where the tachyarrhythmia originates. However, there is a need to locate where the tachyarrhythmia originates when the atrial depolarizations and the ventricular depolarizations present a one-to-one (1:1) relationship.

SUMMARY

An implantable medical device includes a tachyarrhythmia detection and classification system that classifies tachyarrhythmias based on a morphological analysis of template and arrhythmic waveforms. The morphological analysis takes effect of heart rate on the morphological characteristics of the template and arrhythmic waveforms into consideration. Correlation between morphological features of the template waveform and corresponding morphological features of an arrhythmic waveform provides for the basis for classifying the tachyarrhythmia.

In one embodiment, a system for classifying cardiac arrhythmias includes a template waveform input, an arrhythmic waveform input, an arrhythmic heart rate input, a rate-dependent feature locator, and a feature extracting module. The template waveform input receives template data representative of a template waveform. The template waveform is associated with a template heart beat of a known cardiac rhythm. The arrhythmic waveform input receives arrhythmic data representative of an arrhythmic waveform. The arrhythmic waveform is associated with an arrhythmic heart beat of an arrhythmia episode. The arrhythmic heart rate input receives an arrhythmic heart rate parameter that is representative of an arrhythmic heart rate. The arrhythmic heart rate is a heart rate associated with the arrhythmic waveform. The rate-dependent feature locator determines morphological feature locations, including template feature locations and arrhythmic feature locations, using at least the arrhythmic heart rate parameter. The template feature locations are locations of a plurality of template morphological features on the template waveform. The arrhythmic feature locations are locations of a plurality of arrhythmic morphological features on the arrhythmic waveform. The arrhythmic morphological features each correspond to one of the template morphological features. The feature extracting module extracts the plurality of template morphological features from the template waveform at the template feature locations and the plurality of corresponding arrhythmic morphological features from an arrhythmic waveform at the arrhythmic feature locations.

In one embodiment, a method for extracting features in a rate-dependent morphology-based cardiac arrhythmia classification is provided. In response to a detection of an arrhythmia episode, a heart rate parameter representative of an arrhythmic heart rate associated with the arrhythmic episode is produced. Morphological feature locations are determined using at least the heart rate parameter. The morphological feature locations include template feature locations and arrhythmic feature locations. The template feature locations are locations of a plurality of template morphological features on a template waveform associated with a template heart beat of a known cardiac rhythm. The arrhythmic feature locations are locations of a plurality of corresponding arrhythmic morphological features on an arrhythmic waveform associated with an arrhythmic heart beat of the arrhythmia episode. The plurality of template morphological features is extracted from the template waveform at the template feature locations. The plurality of corresponding arrhythmic morphological features is extracted from the arrhythmic waveform at the arrhythmic feature locations.

In one embodiment, a system for classifying cardiac arrhythmias includes a template feature input, an arrhythmic feature input, an arrhythmic heart rate input, a rate-dependent weighting module, and a correlation coefficient calculator. The template feature input receives a plurality of template morphological features of a template waveform associated with a template heart beat of a known cardiac rhythm. The arrhythmic feature input receives a plurality of arrhythmic morphological features of an arrhythmic waveform associated with an arrhythmic heart beat of an arrhythmia episode. The arrhythmic morphological features each correspond to one of the template morphological features. The arrhythmic heart rate input receives an arrhythmic heart rate parameter representative of an arrhythmic heart rate associated with the arrhythmic waveform. The rate-dependent weighting module produces weighted template morphological features and weighted arrhythmic morphological features using at least the plurality of template morphological features, the plurality of arrhythmic morphological features, and the arrhythmic heart rate parameter. The correlation coefficient calculator calculates at least one correlation coefficient representative of a correlation between the weighted arrhythmic morphological features and the weighted template morphological features.

In one embodiment, a method for rate-dependent cardiac arrhythmia classification using weighted morphological features of a cardiac signal is provided. A plurality of template morphological features of a template waveform is received. The template waveform is associated with a template heart beat of a known cardiac rhythm. A plurality of arrhythmic morphological features of an arrhythmic waveform is received. The arrhythmic waveform is associated with an arrhythmic heart beat of an arrhythmia episode. The arrhythmic morphological features each correspond to one of the template morphological features. An arrhythmic heart rate parameter representative of an arrhythmic heart rate associated with the arrhythmic waveform is also received. A plurality of weighting factors is produced using at least the arrhythmic heart rate parameter. Weighted template morphological features and weighted arrhythmic morphological features are produced by applying a weighting factor of the plurality of weighting factors to each of the template morphological features and each of the arrhythmic morphological features. A correlation between the weighted template morphological features and the weighted arrhythmic morphological features is analyzed. The arrhythmia episode is classified based on the correlation.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
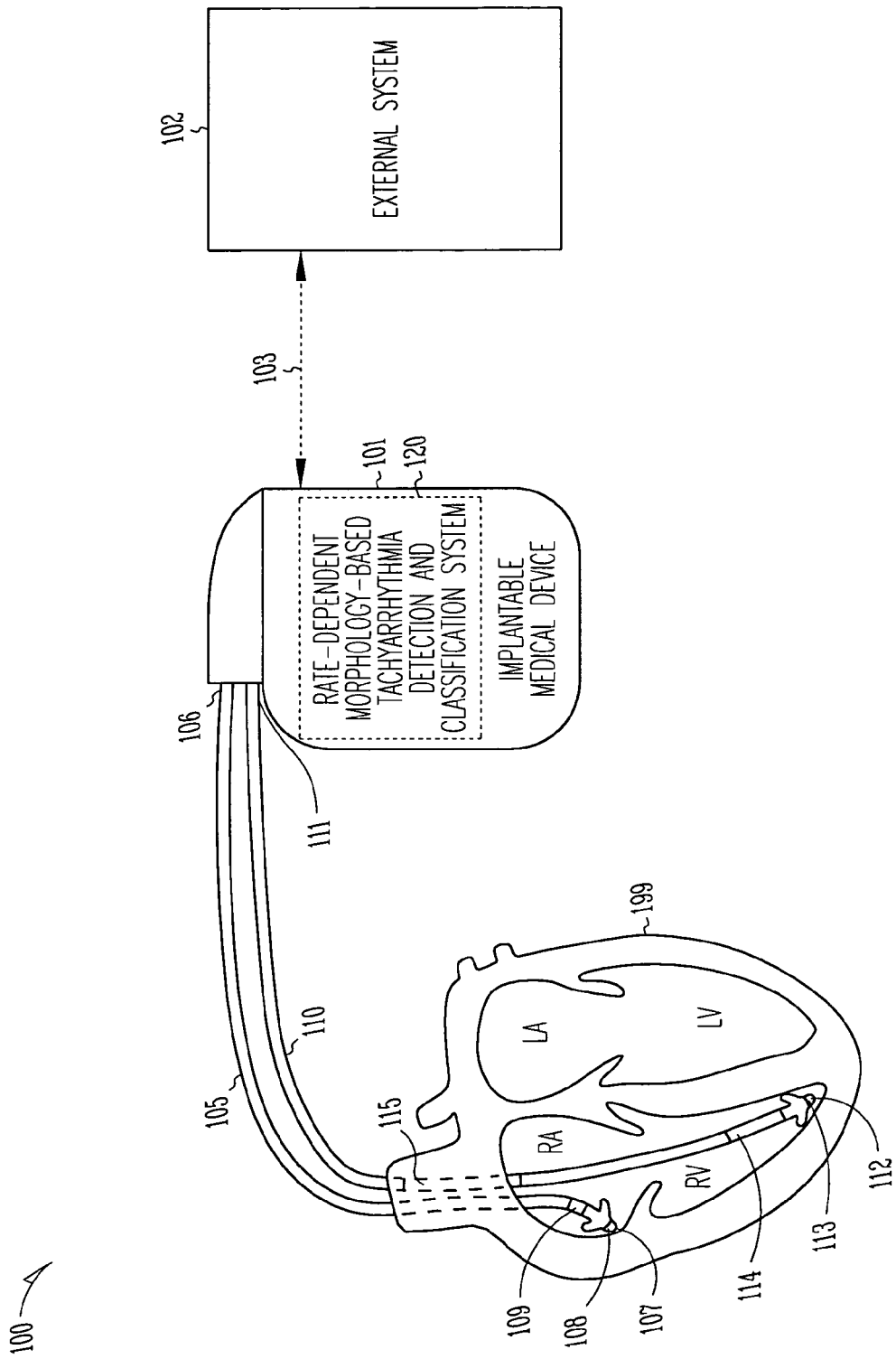
FIG. 1 is an illustration of one embodiment of a CRM system and portions of the environment in which CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

In this document, an "arrhythmic heart beat" includes a heart beat sensed during a detected tachyarrhythmia episode. An "arrhythmic waveform" includes a waveform (such as a segment of an electrogram) associated with an arrhythmic heart beat or any type of representation of that waveform. "Arrhythmic morphological features" include morphological features of an arrhythmic waveform or any type of representation of the morphological features of the arrhythmic waveform. In a specific example, each arrhythmic morphological feature is represented by an amplitude of the arrhythmic waveform measured at the location of that arrhythmic morphological feature. A "template heart beat" represents a heart beat associated with a known cardiac rhythm and used as a "template" for a morphological analysis using morphological features associated with the known rhythm. In one embodiment, the template heart beat is produced from a plurality of hearts beats sensed during the known rhythm, such as by averaging. A "template waveform" includes a waveform associated with the template heart beat or any type of representation of that waveform. "Template morphological features" include morphological features of the template waveform or any type of representation of the morphological features of the template waveform. In a specific example, each template morphological feature is represented by an amplitude of the template waveform measured at the location of that template morphological feature.

The relationship between a heart rate and a cardiac interval (also known as cardiac cycle length), as used in this document, is the relationship between a frequency and its corresponding period. If a heart rate is given in beats per minute (bpm), its corresponding cardiac interval in milliseconds is calculated by dividing 60,000 by the heart rate (where 60,000 is the number of milliseconds in a minute). Any process, such as a comparison, using a heart rate is to be modified accordingly when a cardiac interval is used instead. For example, if a tachyarrhythmia is detected when the ventricular rate exceeds a tachyarrhythmia threshold rate, an equivalent process is to detect the tachyarrhythmia when the ventricular interval falls below a tachyarrhythmia threshold interval. The appended claims should be construed to cover such variations.

This document discusses, among other things, a CRM system including a circuit for further classifying a detected cardiac arrhythmia including, but not being limited to, a 1:1 tachyarrhythmia. The 1:1 tachyarrhythmia, characterized by an approximately one-to-one association between atrial and ventricular depolarizations, is indicated by substantially equal atrial and ventricular rates. The 1:1 tachyarrhythmia is further classified based on a morphological analysis of template and arrhythmic waveforms each being a segment of a cardiac signal such as an electrogram. The present subject provides for a rate-dependent morphological analysis which takes the effect of heart rate in the morphology of the template and arrhythmic waveforms into consideration. The morphological analysis analyzes the correlation between morphological features extracted from the template and arrhythmic waveforms. The 1:1 tachyarrhythmia is classified based on the correlation. In one embodiment, the morphological analysis includes a rate-dependent feature extraction, in which the morphological features are extracted from the template and arrhythmic waveforms at locations on these waveforms determined by at least the heart rate associated with the arrhythmic waveform. In another embodiment, the relative weight of each morphological feature used in the correlation analysis is a function of at least the heart rate associated with the arrhythmic waveform. It is to be understood that while the classification of the 1:1 tachyarrhythmia is specifically discussed throughout this document as examples, the methods and apparatuses of the present subject matter are also applicable in morphology-based classification of cardiac arrhythmias other than the 1:1 tachyarrhythmia.

FIG. 1 is an illustration of one embodiment of a CRM system 100 and portions of the environment in which CRM system 100 operates. CRM system 100 includes an implantable medical device 101 that is electrically coupled to a heart 199 through leads 105 and 110. An external system 102 communicates with implantable medical device 101 via a telemetry link 103. In one embodiment, implantable medical device 101 is an ICD. In a specific embodiment, implantable medical device 101 is an ICD that has pacing capabilities. In various embodiments, implantable medical device 101 includes a cardioversion/defibrillation circuit and one or more additional therapeutic and/or monitoring circuits and/or devices. Examples of such therapeutic and/or monitoring circuits and/or devices include a pacing circuit, a neural stimulation circuit, a drug delivery device, a drug delivery controller, a biologic therapy delivery device, and a biologic therapy controller.

Implantable medical device 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is a pacing lead that includes a proximal end 106 connected to implantable medical device 101 and a distal end 107 disposed in the right atrium (RA) of heart 199. A pacing-sensing electrode 108 is located at distal end 107. Another pacing-sensing electrode 109 is located near distal end 107. Electrodes 108 and 109 are electronically connected to implantable medical device 101 via separate conductors in lead 105 to allow sensing of the atrial electrogram and/or delivery of atrial pacing pulses. Lead 110 is a defibrillation lead that includes a proximal end 111 connected to implantable medical device 101 and a distal end 112 disposed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to implantable medical device 101 via separate conductors in lead 110. Electrode 113 allows sensing of the ventricular electrogram and/or delivery of ventricular pacing pulses. Electrodes 114 and 115 allow delivery of ventricular cardioversion/defibrillation pulses. In various embodiments, system 101 includes one or more leads each including one or more electrodes, depending on the requirements of the intended therapy.

Implantable medical device 101 includes a rate-dependent morphology-based tachyarrhythmia detection and classification system 120 that includes a rate-dependent morphology-based 1:1 tachyarrhythmia discrimination module. An embodiment of a circuit of system 120 is discussed below with reference to FIG. 2. System 120 detects and classifies 1:1 tachyarrhythmias by using a rate-dependent morphology-based 1:1 tachyarrhythmia discrimination method introduced below with reference to FIG. 3. Depending on the outcome of the tachyarrhythmia detection and classification, system 120 determines whether to deliver a pacing and/or cardioversion/defibrillation therapy. In one embodiment, system 120 delivers a ventricular defibrillation pulse when a 1:1 tachyarrhythmia is classified as a VT.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system allows access to implantable medical device 101 from a remote location, such as for monitoring patient status and adjusting therapies. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), programming implantable medical device 101 to run a signal analysis algorithm (such as an algorithm implementing the morphology-based 1:1 tachyarrhythmia discrimination method discussed in this document), and programming implantable medical device 101 to deliver pacing and/or cardioversion/defibrillation therapies.

Figure 2:
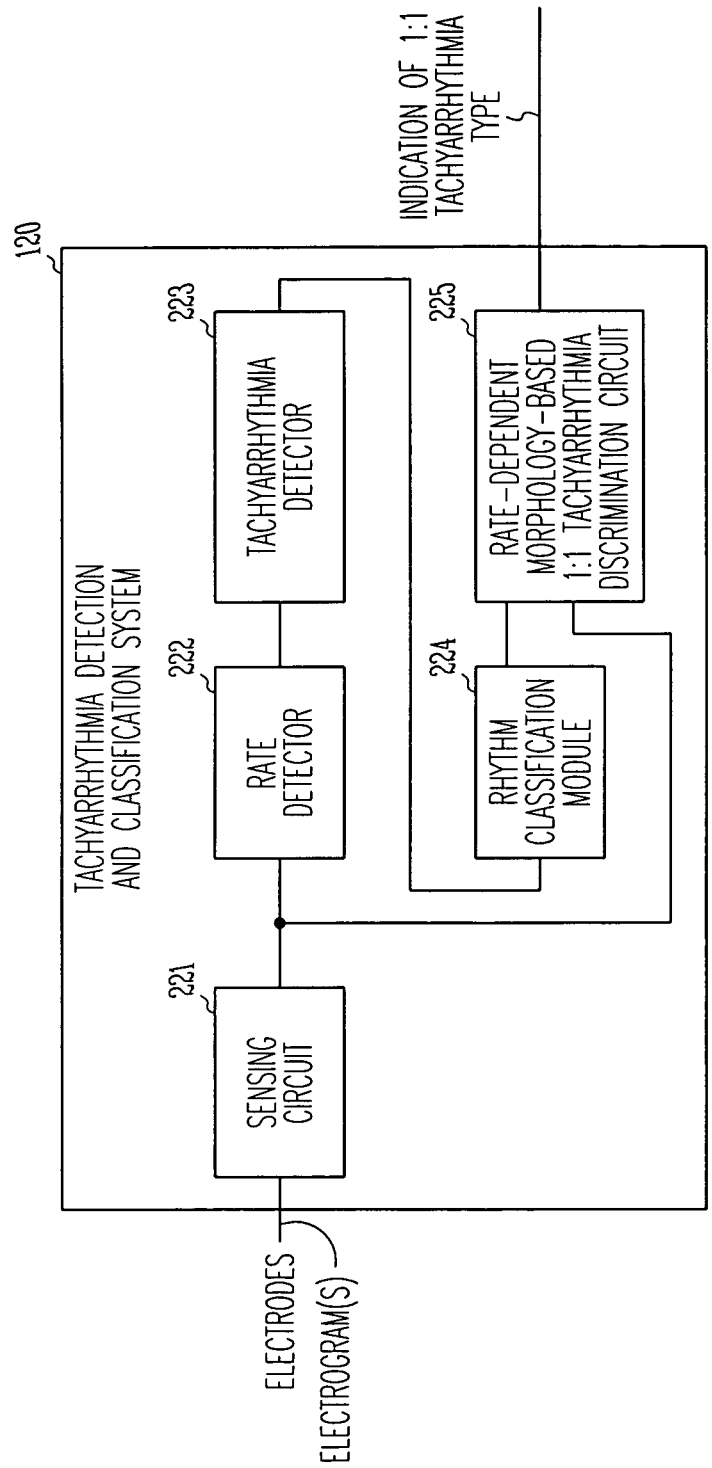
FIG. 2 is a block diagram illustrating an embodiment of a tachyarrhythmia detection and classification system being part of the CRM system.

FIG. 2 is a block diagram illustrating an embodiment of a circuit of system 120. System 120 includes a sensing circuit 221, a rate detector 222, a tachyarrhythmia detector 223, a rhythm classification module 224, and a rate-dependent morphology-based 1:1 tachyarrhythmia discrimination module 225. Sensing circuit 221 is electrically coupled to heart 199 to sense an atrial electrogram and a ventricular electrogram. The atrial electrogram includes atrial events each indicative of an atrial depolarization, also known as a P-wave. The ventricular electrogram includes ventricular events each indicative of a ventricular depolarization, also known an R-wave. Rate detector 222 detects an atrial rate based on the atrial electrogram and a ventricular rate based on the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute. Tachyarrhythmia detector 223 detects a tachyarrhythmia based on at least one of the atrial rate and the ventricular rate. In one embodiment, the tachyarrhythmia is detected when the atrial rate exceeds a predetermined tachyarrhythmia threshold rate. In another embodiment, the tachyarrhythmia is detected when the ventricular rate exceeds a predetermined tachyarrhythmia threshold rate. Rhythm classification module 224 classifies the detected tachyarrhythmia as a 1:1 tachyarrhythmia when the atrial rate and the ventricular rate are substantially equal. In one embodiment, rhythm classification module 224 classifies the detected tachyarrhythmia as the 1:1 tachyarrhythmia when the difference between the atrial rate and the ventricular rate is between a predetermined limit, such as 10 bpm. Rate-dependent morphology-based 1:1 tachyarrhythmia discrimination module 225 further classifies the 1:1 tachyarrhythmia, such as by its origin, by performing one or more methods for morphology-based tachyarrhythmia discrimination discussed in this document.

Figure 3:
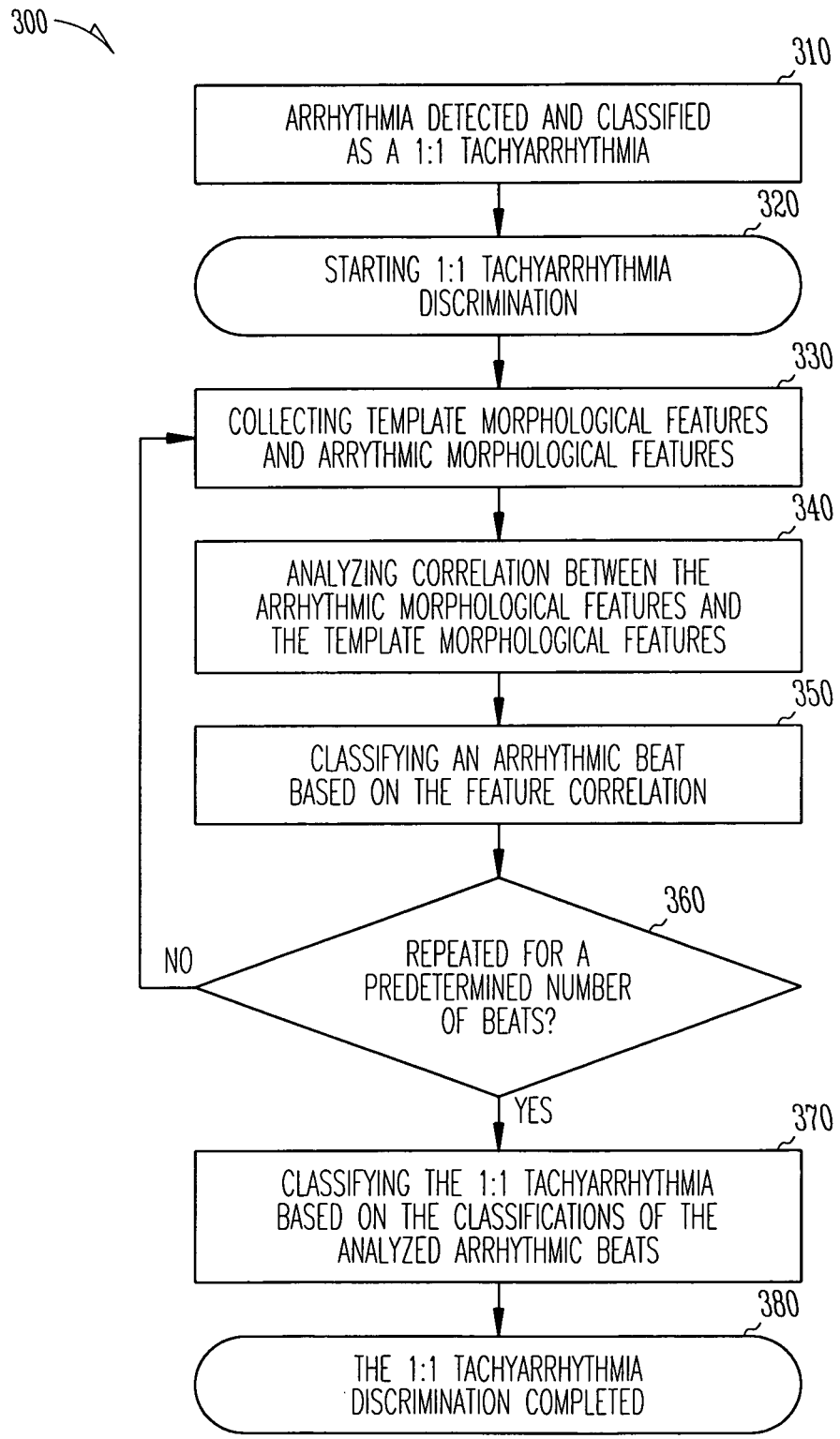
FIG. 3 is a flow chart illustrating an embodiment of a method for rate-dependent morphology-based 1:1 tachyarrhythmia discrimination.

FIG. 3 is a flow chart illustrating an embodiment of a method 300 for morphology-based tachyarrhythmia discrimination. In one embodiment, method 300 is performed by rate dependent, morphology-based 1:1 tachyarrhythmia discrimination module 225. After a detected arrhythmia is classified as a 1:1 tachyarrhythmia at 310, a process of discriminating the 1:1 tachyarrhythmia is started at 320.

Template morphological features and arrhythmic morphological features are collected at 330. The morphological features are points in a cardiac signal that have morphological characteristics allowing discrimination between two or more types of 1:1 tachyarrhythmias. A plurality of template morphological features is collected from a template waveform of a template heart beat and represents that template waveform. A plurality of arrhythmic morphological features is collected from an arrhythmic waveform of an arrhythmic heart beat and represents that arrhythmic waveform. In one embodiment, the template heart beat represents a heart beat of a normal sinus rhythm (NSR).

In one embodiment, static feature locations on the template and arrhythmic waveforms are used for the feature collections. The feature locations are predetermined and remain static (i.e., rate-independent) during the morphology-based tachyarrhythmia discrimination. That is, locations of template morphological features on a template waveform and corresponding locations of arrhythmic morphological features on the arrhythmic waveform are predetermined at the time when the template morphological features are extracted from the template waveform and stored. The collection of the template morphological features includes recording timing and other quantitative information, such as amplitudes, associated with the features. In one specific embodiment, the collection of the template morphological features is repeated for a plurality of template heart beats, and the timing and other quantitative information associated with the features are averages calculated over the plurality of template heart beats. For discriminating the detected 1:1 tachyarrhythmia, arrhythmic morphological features are extracted from the arrhythmic waveform by temporal correspondence with the template morphological features. In one embodiment, a template fiducial point is located on the template waveform. The template morphological features are located using the template fiducial point and predetermined time intervals each between one of the template morphological features and the template fiducial point. An arrhythmic fiducial point is located on the arrhythmic waveform. The arrhythmic fiducial point corresponds to the template fiducial point. In a specific embodiment, the template fiducial point is the peak of R wave on the template waveform, and the arrhythmic fiducial point is the peak of R wave on the arrhythmic waveform. The arrhythmic morphological features are located using the arrhythmic fiducial point and the predetermined time intervals each between one of the arrhythmic morphological features and the arrhythmic fiducial point. Then, the located arrhythmic morphological features are extracted from the arrhythmic waveform. A plurality template morphological features and a plurality of corresponding arrhythmic morphological features are thus collected for the correlation analysis that follows.

In another embodiment, rate-dependent feature locations on the template and arrhythmic waveforms are used for the feature collections. The feature locations are dynamically determined during the morphology-based tachyarrhythmia discrimination, based on a heart rate associated with the tachyarrhythmia being discriminated. When the heart rate associated with the arrhythmic waveform is substantially higher than the heart rate associated with the template waveform, the temporal correspondence between the template and arrhythmic waveforms may not translate to morphological correspondence. A possible consequence is an erroneous VT classification when the detected tachyarrhythmia is actually an SVT induced by exercise. The rate-dependent feature locations are determined at the time when an arrhythmia episode is detected and being classified. Locations of template morphological features on the template waveform and corresponding locations of arrhythmic morphological features on the arrhythmic waveform are dynamically determined based on the instantaneous heart rate associated with the arrhythmic waveform. A template waveform is stored using a data resolution that is sufficiently high to allow feature extraction at dynamically determined feature locations. When an arrhythmia episode is detected, feature locations are each determined as a function of at least the arrhythmic heart rate associated with the arrhythmic waveform. Template morphological features are extracted from the stored template waveform, and arrhythmic morphological features are extracted from the arrhythmic waveform, at these dynamically determined, rate-dependent feature locations. This rate-dependent feature extraction reduces or minimizes the effect of heart rate in the morphological correspondence between the template morphological features and the arrhythmic morphological features. In an alternative embodiment, the heart rate associated with the arrhythmic waveform is represented by a heart rate zone. Each heart rate zone includes a predetermined range of heart rates. This reduces the computation required to determine the feature locations and the resolution (number of samples) required for the stored template waveform. This dynamic, rate-dependent morphological feature extraction is discussed in detail below, with reference to FIGS. 5-8.

Correlation between the arrhythmic morphological features and the template morphological features is analyzed at 340. The correlation analysis results in one or more correlation coefficients associated with each arrhythmic heart beat. One example for calculating such a correlation coefficient, referred to as a feature correlation coefficient (Fcc), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety.

In one embodiment, in which the template and arrhythmic morphological features are extracted using the static feature locations, the morphological features are weighted before the one or more correlation coefficients are calculated. A weighting factor being a function of the arrhythmic heart rate is applied to each template morphological feature and corresponding arrhythmic morphological feature. Such weighting factors are predetermined to give relatively more weights to the morphological features extracted from portions of the waveform where the heart rate has relatively insubstantial effect on the morphology. This rate-dependent correlation analysis is discussed in detail below, with reference to FIGS. 9-12.

The arrhythmic heart beat is classified based on the one or more correlation coefficients at 350. In one embodiment, each correlation coefficient is compared to one or more thresholds defining detection windows each corresponding to one type of 1:1 tachyarrhythmia. In another embodiment, a score is produced based on the one or more correlation coefficients to provide a measure of the probability that the 1:1 tachyarrhythmia is of a known particular type. Examples of the known particular types of 1:1 tachyarrhythmia include, but are not limited to, supraventricular tachyarrhythmia (SVT), ventricular tachyarrhythmia (VT), monomorphic VT (MVT), and polymorphic VT (PVT).

The feature collection and correlation are repeated for a predetermined number of arrhythmic heart beats. If the predetermined number has not been reached at 350, steps 330 through 340 are repeated for the next arrhythmic heart beat.

After the predetermined number has been reached at 360, the 1:1 tachyarrhythmia is classified based on the classification given to the analyzed arrhythmic heart beats at 370. In one embodiment, the 1:1 tachyarrhythmia is classified by a majority voting. That is, the 1:1 tachyarrhythmia is classified as a tachyarrhythmia of a particular type if a majority of the analyzed arrhythmic heart beats are classified as the tachyarrhythmia of that particular type. In one specific embodiment, 80% (such as 8 out of 10 analyzed arrhythmic heart beats) is considered as the majority. For example, to discriminate between VT and SVT using an NSR beat as the template heart beat, if 8 out of 10 arrhythmic heart beats are classified as VT beats, the tachyarrhythmia is classified as a VT rhythm. Otherwise, it is classified as a SVT rhythm. In another specific embodiment, 60% is considered as the majority. In another embodiment, in which a score is produced to provide a measure of the likeliness that the 1:1 tachyarrhythmia is of a known particular type, the scores produced for all the analyzed arrhythmic heart beats are averaged or otherwise processed to provide an indication for the type of the 1:1 tachyarrhythmia.

The discrimination of the 1:1 tachyarrhythmia is completed at 380, with a classification of the 1:1 tachyarrhythmia being indicated. In one embodiment, the classification provides for a basis for making a therapeutic decision. For example, if a 1:1 tachyarrhythmia is classified as a VT, a ventricular defibrillation pulse is delivered.

Figure 4:
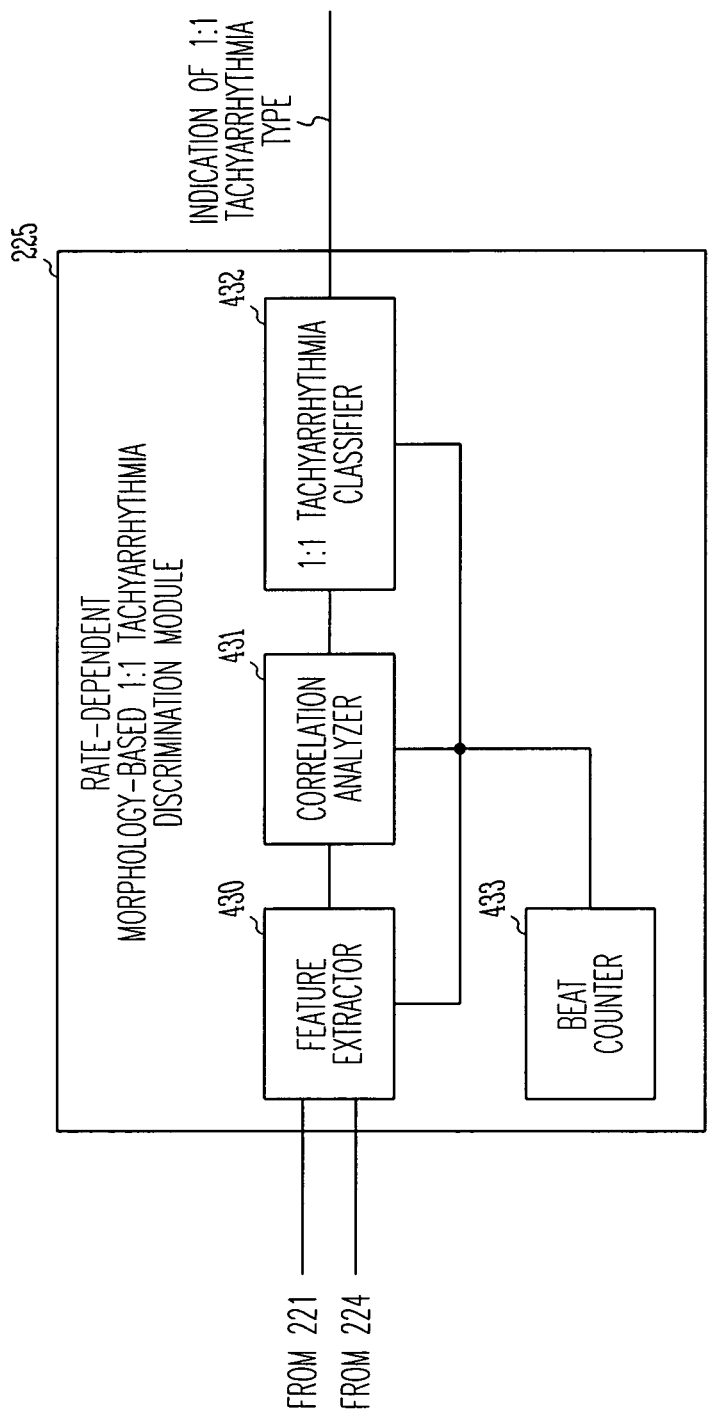
FIG. 4 is a block diagram illustrating an embodiment of a rate-dependent morphology-based 1:1 tachyarrhythmia discrimination module being part of the tachyarrhythmia detection and classification system.

FIG. 4 is a block diagram illustrating an embodiment of rate-dependent morphology-based 1:1 tachyarrhythmia discrimination module 225. Rate-dependent morphology-based 1:1 tachyarrhythmia discrimination module 225 includes a feature extractor 430, a correlation analyzer 431, a 1:1 tachyarrhythmia classifier 432, and a beat counter 433. Feature extractor 430 extracts features a waveform associated with a heart beat. Correlation analyzer 431 computes a correlation coefficient between arrhythmic morphological features of an arrhythmic beat of a 1:1 tachyarrhythmia and template morphological features of a beat of a known cardiac rhythm. In one embodiment, correlation analyzer 431 computes the feature correlation coefficient (Fcc) for each arrhythmic beat of a plurality of arrhythmic beats sensed during a detected tachyarrhythmia. Beat counter 433 counts the number of arrhythmic heart beats for which the arrhythmic features are extracted and analyzed. Based on the correlation coefficients calculated for a predetermined number of arrhythmic heart beats, 1:1 tachyarrhythmia classifier 432 classifies the 1:1 tachyarrhythmia.

Rate-dependent morphology-based arrhythmia classification module 225 classifies a detected arrhythmia episode by producing one or more correlation coefficients indicative of a correlation between a template waveform and an arrhythmic waveform using the template waveform and the arrhythmic waveform as well as an arrhythmic heart rate parameter associated with the arrhythmic waveform. The template waveform represents a template heart beat of a known cardiac rhythm, such as an NSR. The arrhythmic waveform represents an arrhythmic heart beat of the detected arrhythmia episode. In one embodiment, rate-dependent morphology-based 1:1 tachyarrhythmia discrimination module 225 performs the method illustrated in FIG. 3. Feature extractor 430 performs step 330, correlation analyzer 431 performs step 340, and 1:1 tachyarrhythmia classifier 432 performs step 360. In a specific embodiment, feature extractor 430 is a rate-dependent feature extractor that performs the dynamic, rate-dependent morphological feature extraction, and correlation analyzer 431 performs the correlation analysis using the extracted morphological features without applying the weighting factors. In another specific embodiment, feature extractor 430 performs the static, rate-independent morphological feature extraction, and correlation analyzer 431 is a rate-dependent correlation analyzer that performs the rate-dependant correlation analysis by applying the weighting factors to the extracted morphological features before calculating the one or more correlation coefficient.

Rate-Dependent Feature Extraction

FIGS. 5A-D illustrate various embodiments of rate-dependent feature extraction for discrimination of the 1:1 tachyarrhythmia. These various embodiments of rate-dependent feature extraction each represent a specific embodiment of step 330 of method 300 illustrated in FIG. 3. FIGS. 5A-D each illustrate a template wave form 500 with template morphological features (each labeled as Fn or Fn'). The template feature locations (locations for the template morphological features on the template waveform) are used to locate corresponding arrhythmic feature locations (locations for the template morphological features on the arrhythmic waveform) by temporal alignment. The arrhythmic waveform is temporally aligned with template waveform 500. The template morphological features and the corresponding arrhythmic morphological features are temporally aligned in pairs.

Figure 5A:
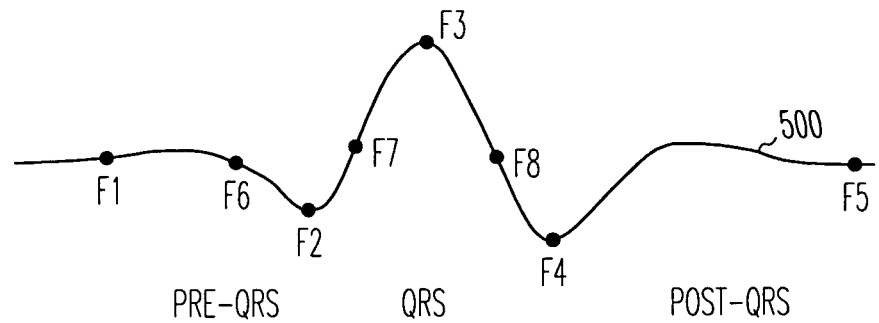
FIGS. 5A-D illustrate various embodiments of a method for rate-dependent feature extraction for discrimination of 1:1 tachyarrhythmia.
Figure 5B:
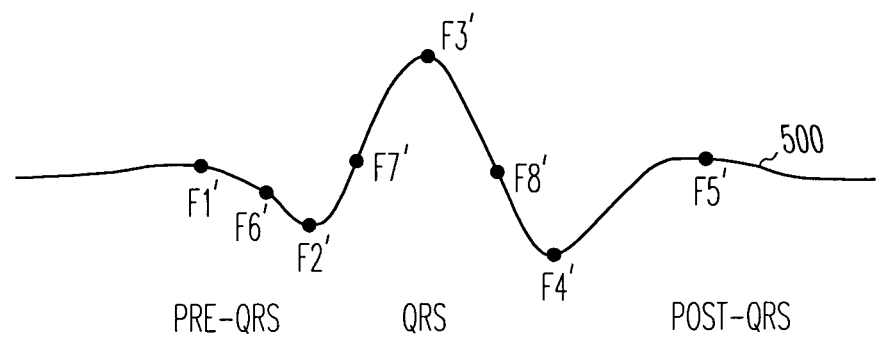
Figure 5C:
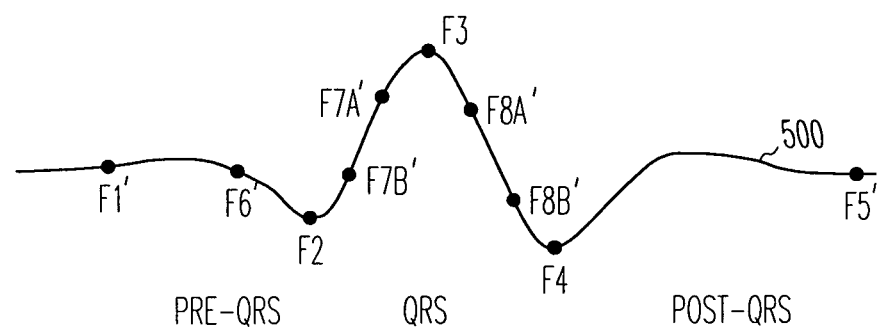
Figure 5D:
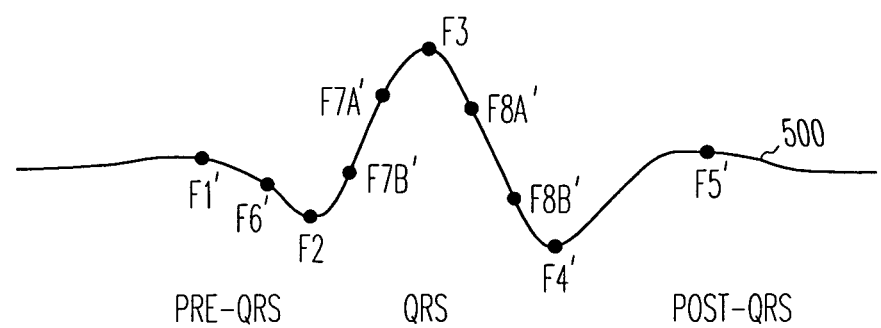

FIG. 5A illustrates a set of template morphological features (each labeled as Fn) located for a relatively low template heart rate, while FIGS. 5B-D each illustrate a set of template morphological features (each labeled as Fn') located for a relatively high arrhythmic heart rate. Template waveform 500 is divided into multiple segments (or regions) including a pre-QRS segment, a QRS segment, and a post-QRS segment. The QRS segment correspond to the QRS complex included in template waveform 500. Template morphological features F2/F2' and F4/F4' serve as anchor points that divide template waveform 500, where F2/F2' is associated with the beginning of the QRS complex and F4/F4' is associated with the end of the QRS complex.

In one embodiment, as illustrated in FIG. 5B, locations of the template morphological features in the QRS segment do not change, while locations of the template morphological features in the pre-QRS and post-QRS segments move toward the QRS segment. The location of a template morphological feature in the pre-QRS segment is given by:

$$d' = \frac{\alpha}{HR_A},$$

where d' is the distance (time interval) between a template morphological feature in the pre-QRS segment and the anchor point at the beginning of the QRS segment at the arrhythmic heart rate, α is a predetermined constant associated with the template morphological feature, and $HR_A$ is the arrhythmic heart rate. In one embodiment, $$\alpha = d \cdot HR_T,$$

where d is the distance corresponding to d' but at the template heart rate, and $HR_T$ is the template heart rate. The location of a template morphological feature in the post-QRS segment is given by:

$$d' = \frac{\beta}{HR_A},$$

where d' is the distance (time interval) between a template morphological feature in the post-QRS segment and the anchor point at the end of the QRS segment at the arrhythmic heart rate, β is a predetermined constant, and $HR_A$ is the arrhythmic heart rate. In one embodiment, $$\beta = d \cdot HR_T,$$

where d is the distance corresponding to d' but at the template heart rate, and $HR_T$ is the template heart rate. In general, locations of a template morphological feature in the pre-QRS and post-QRS segments are each given by:

$$d' = d \frac{HR_T}{HR_A},$$

where d' is the distance (time interval) between a template morphological feature in the pre-QRS segment and the anchor point at the beginning of the QRS segment or between a template morphological feature in the post-QRS segment and the anchor point at the end of the QRS segment at the arrhythmic heart rate, d is the corresponding distance at the template heart rate, $HR_T$ is the template heart rate, and $HR_A$ is the arrhythmic heart rate. For example, $$d'_{12} = d_{12} \frac{HR_T}{HR_A},$$

where $d'_{12}$ is the distance between template morphological features F1' and F2' (as seen in FIG. 5B), and $d_{12}$ is the distance between template morphological features F1 and F2 (as seen in FIG. 5A); and $$d'_{54} = d_{54} \frac{HR_T}{HR_A},$$

where $d'_{54}$ is the distance between template morphological features F5' and F4' (as seen in FIG. 5B), and $d_{54}$ is the distance between template morphological features F5 and F4 (as seen in FIG. 5A). Locations of F2/F2' and F4/F4' do not change with the heart rate. Therefore, at the arrhythmic heart rate, location of F1' is given by $d'_{12}$, and location of F5' is given by $d'_{54}$.

In another embodiment, as illustrated in FIG. 5C, locations of the template morphological features in the pre-QRS and post-QRS segments do not change, while more template morphological features are extracted in the QRS segment. In one embodiment, F3/F3', which is associated with the peak of the R wave, is used as another anchor point. Locations of the anchor points, including those corresponding to the beginning (F2/F2'), the peak (F3/F3'), and the end (F4/F4') of the QRS segment, do not change with the heart rate. That is, the locations of these anchor points are used as locations of the template morphological features at any heart rate. On the other hand, quantity and locations of other template morphological features in the QRS segment are dependent on the arrhythmic heart rate. In one embodiment, the template morphological features in the QRS segment are substantially evenly distributed in the QRS region. In another embodiment, the template morphological features between the beginning and the peak of the QRS segment are substantially evenly distributed between the beginning and the peak of the QRS segment, and the template morphological features between the peak and the end of the QRS segment are substantially evenly distributed between the peak and the end of the QRS segment. For example, as illustrated in FIG. 5A, at the template heart rate, five template morphological features (F2, F7, F3, F8, and F4) are located in the QRS segment. As illustrated in FIG. 5C, at the arrhythmic heart rate, seven template morphological features (F2', F7B', F7A', F3', F8A', F8B', and F4') are located in the QRS segment. Locations for F2/F2', F3/F3', and F4/F4' are kept unchanged at different heart rates. The number of template morphological features between F2/F2' and F3/F3' and the number of template morphological features between F3/F3' and F4/F4' are doubled.

In another embodiment, as illustrated in FIG. 5D, more template morphological features are extracted in the QRS segment, and locations of the template morphological features in the pre-QRS and post-QRS segments move toward the QRS segment. In other words, the method for locating template morphological features illustrated in FIG. 5D is a combination of the methods illustrated in FIGS. 5B and 5C.

Figure 6:
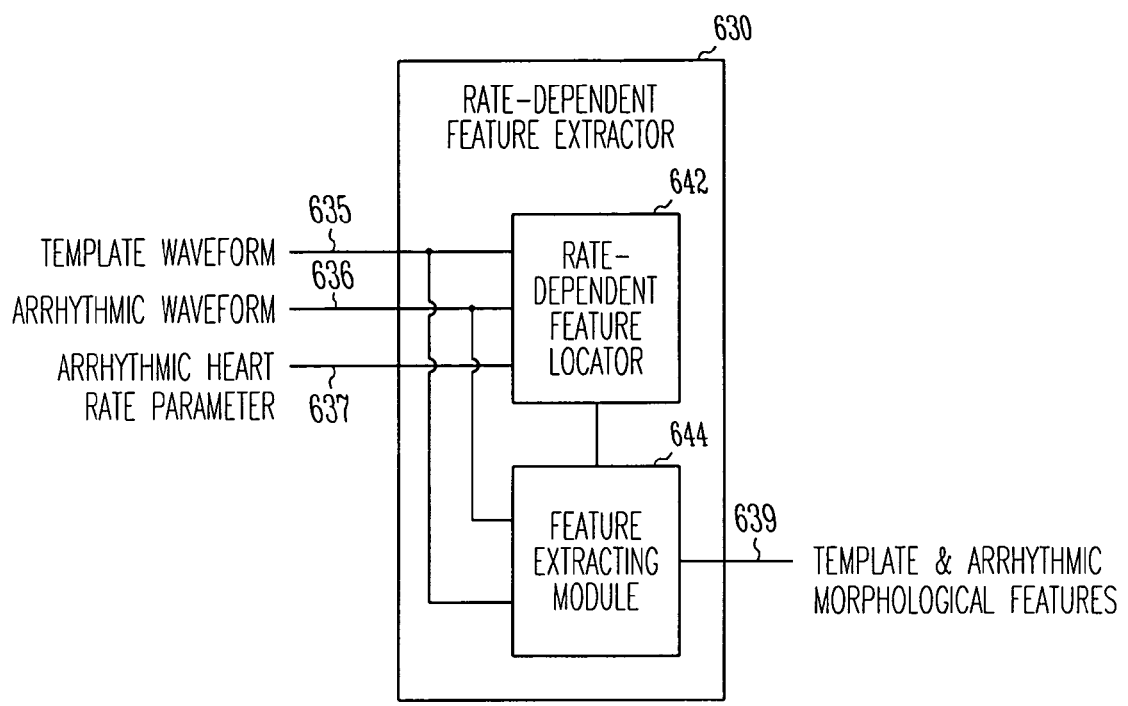
FIG. 6 is a block diagram illustrating an embodiment of a rate-dependent feature extractor being part of the rate-dependent morphology-based 1:1 tachyarrhythmia discrimination module.

FIG. 6 is a block diagram illustrating an embodiment of a rate-dependent feature extractor 630, which is a specific embodiment of feature extractor 430. Rate-dependent feature extractor 630 includes a template waveform input 635, an arrhythmic waveform input 636, an arrhythmic heart rate input 637, a rate-dependent feature locator 642, a feature extracting module 644, and a feature output 639. Template waveform input 635 receives template data representative of a template waveform associated with a template heart beat of a known cardiac rhythm, such as an NSR. Arrhythmic waveform input 636 receives arrhythmic data representative of an arrhythmic waveform associated with an arrhythmic heart beat of an arrhythmia episode. Arrhythmic heart rate input 637 receives an arrhythmic heart rate parameter representative of an arrhythmic heart rate associated with the arrhythmic waveform. Rate-dependent feature locator 642 determines morphological feature locations using at least the arrhythmic heart rate parameter. The morphological feature locations include template feature locations of a plurality of template morphological features on the template waveform and arrhythmic feature locations of a plurality of corresponding arrhythmic morphological features on the arrhythmic waveform. Feature extracting module 644 extracts the plurality of template morphological features from the template waveform and the plurality of corresponding arrhythmic morphological features from an arrhythmic waveform based on the morphological feature locations determined by rate-dependent feature locator 642. Feature output 639 outputs data representative of the plurality of template morphological features and the plurality of corresponding arrhythmic morphological features.

Figure 7:
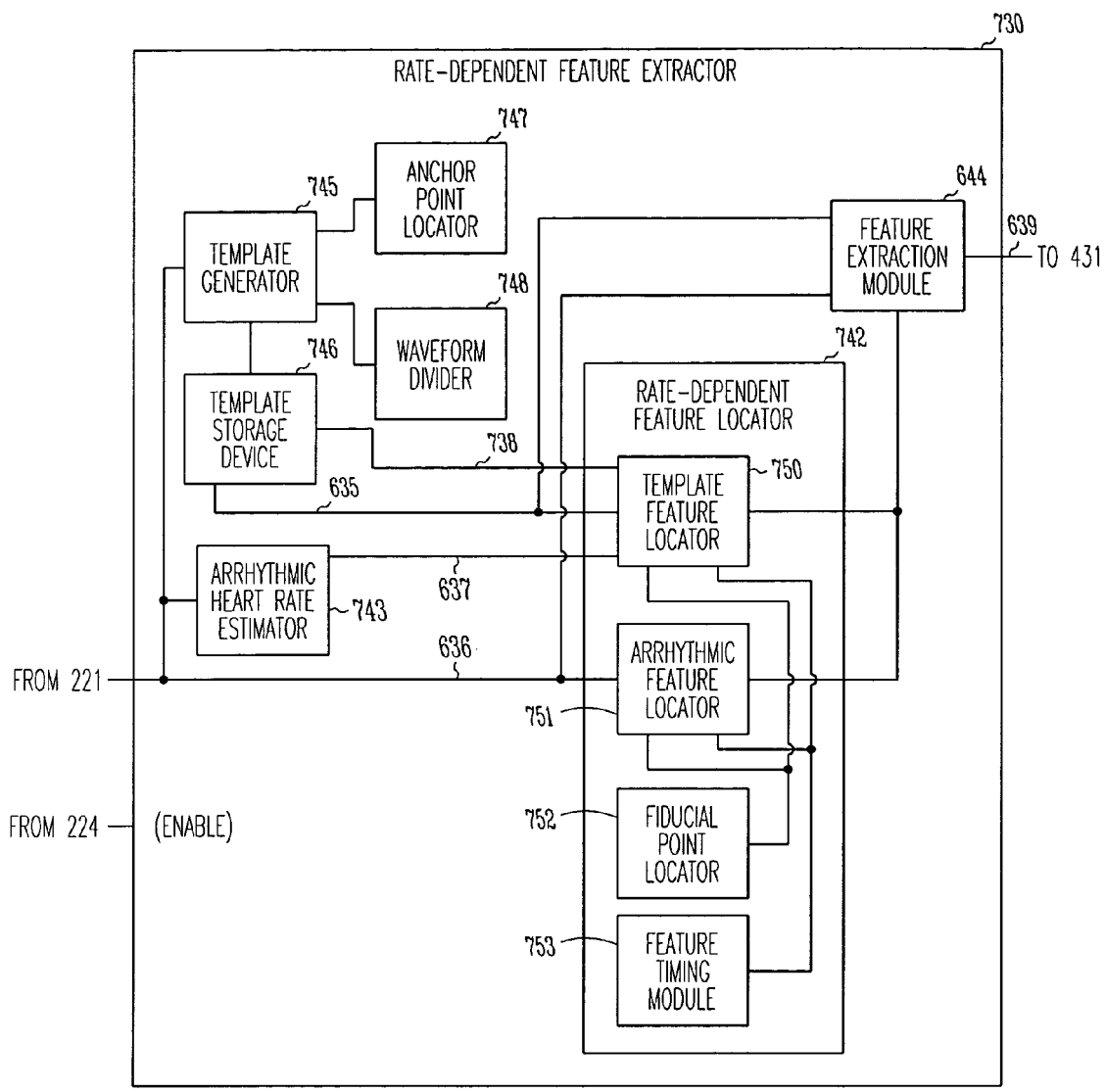
FIG. 7 is a block diagram illustrating a specific embodiment of the rate-dependent feature extractor of FIG. 6.

FIG. 7 is a block diagram illustrating an embodiment of a rate-dependent feature extractor 730, which is a specific embodiment of rate-dependent feature extractor 630. Rate-dependent feature extractor 730 includes a template generation and storage system (including template generator 745, template storage device 746, anchor point locator 747, and waveform divider 748), an arrhythmic heart rate estimator 743, a rate-dependent feature locator 742, and feature extraction module 644. In addition, as illustrated, rate-dependent feature extractor 730 includes template waveform input 635, arrhythmic waveform input 636, arrhythmic heart rate input 637, feature output 639, and a template heart rate input 738 that receives a template heart rate parameter representative of a template heart rate associated with the template waveform.

Template generator 745 produces data representative of the template waveform. In one embodiment, template generator 745 includes an analog-to-digital converter to digitize the template waveform at a sampling frequency in a range between approximately 200 and 1,000 Hz, with approximately 400 Hz being a specific example. The data representative of the template waveform include approximately 64 to 320 samples of the template waveform; with approximately 128 samples being a specific example. In one embodiment, template generator 745 includes a template heart rate parameter generator to produce the template heart rate parameter by measuring the heart rate associated with the template waveform. Anchor point locator 747 locates a plurality of anchor points on the template waveform. Waveform divider 748 divides the template waveform using one or more anchor points of the plurality of anchor points located by anchor point locator. Anchor point locator 747 includes, but is not limited to, one or more of a peak detector (such as an R-wave peak detector), a fiducial point detector, and a turning point detector. In one embodiment, anchor point locator 747 includes a turning point locator that locates a first turning point associated with the beginning of a QRS complex and a second turning point associated with the end of the QRS complex. Waveform divider 748 divides the template waveform into a pre-QRS segment, a QRS segment, and a post-QRS segment using the first and second turning points. Template waveform storage device 746 stores the data representative of the template waveform. In one embodiment, the data include the digitized template waveform as well as information related to the anchor points, waveform segments, and the template heart rate.

Arrhythmic heart rate estimator 743 produces the arrhythmic heart rate parameter by estimating an instantaneous heart rate associated with the arrhythmic heart beat. In one embodiment, the heart rate parameter is a heart rate range that includes the estimated instantaneous heart rate. Arrhythmic heart rate estimator 743 produces the arrhythmic heart rate parameter by estimating the instantaneous heart rate and mapping that instantaneous heart rate to one heart rate range of a plurality of predetermined heart rate ranges. This substantially reduces the amount of computation performed by rate-dependent feature extractor 730 and substantially reduces the resolution required for the digitized template waveform. In one embodiment, the heart rate ranges each have a width of approximately 10 bpm to 50 bpm. In a specific embodiment, the heart rate ranges each have a width of approximately 20 bpm.

Rate-dependent feature locator 742 is a specific embodiment of rate-dependent feature locator 642 and includes a template feature locator 750, an arrhythmic feature locator 751, a fiducial point locator 752, and a feature timing module 753. Template feature locator 750 determines the template feature locations of the plurality of template morphological features using at least the arrhythmic heart rate parameter and one or more selected anchor points of the plurality of anchor points. In one embodiment, template feature locator 750 locate the plurality of template morphological features by performing one of the methods of rate-dependent feature extraction illustrated in FIGS. 5A-D. Fiducial point locator 752 locates a template fiducial point on the template waveform and a corresponding arrhythmic fiducial point on the arrhythmic waveform. The template fiducial point and the corresponding arrhythmic fiducial point are of the same type characteristic point that is present in both waveforms. In a specific embodiment, the template fiducial point is the R-wave peak on the template waveform, and the corresponding arrhythmic fiducial point is the R-wave peak on the arrhythmic waveform. Feature timing module 753 measures feature time intervals each between one template morphological feature of the plurality of template morphological features and the template fiducial point. Arrhythmic feature locator 751 determines the arrhythmic feature locations of the plurality of corresponding arrhythmic morphological features on the arrhythmic waveform using the arrhythmic fiducial point and the measured feature time intervals. The measured time intervals are each used as a time interval between one arrhythmic morphological feature of the plurality of corresponding arrhythmic morphological features and the arrhythmic fiducial point.

Feature extraction module 644 extracts the plurality of template morphological features and the plurality of corresponding arrhythmic morphological features using the feature locations determined by rate-dependent feature locator 742. In one embodiment, each morphological feature is represented by its amplitude. Feature extraction module 644 extracts the plurality of template morphological features by measuring the amplitudes at the template feature locations and extracts the plurality of corresponding arrhythmic morphological features by measuring the amplitudes at the arrhythmic feature locations.

Figure 8:
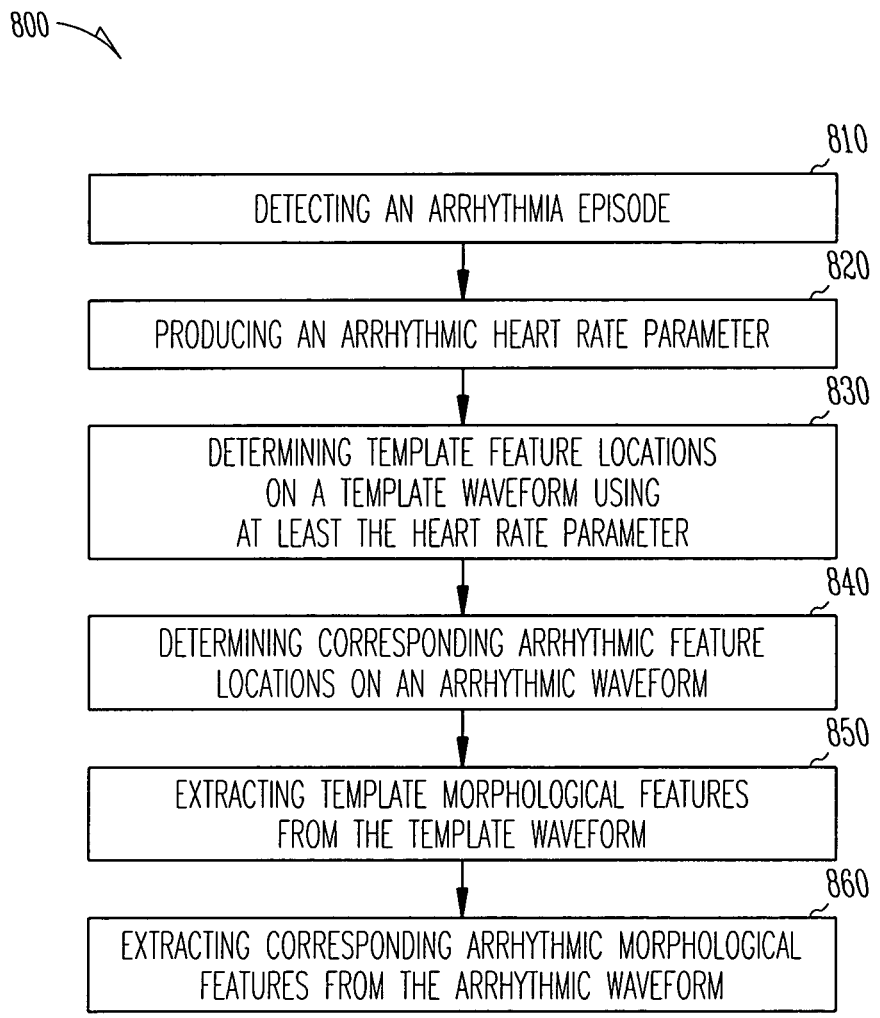
FIG. 8 is a flow chart illustrating an embodiment of a method for rate-dependent feature extraction for discrimination of 1:1 tachyarrhythmia.

FIG. 8 is a flow chart illustrating an embodiment of a method 800 for rate-dependent feature extraction for discrimination of 1:1 tachyarrhythmia. In one embodiment, method 800 is performed by tachycardia detection and classification system 120.

An arrhythmia episode is detected at 810. In one embodiment, method 800 proceeds after 810 if a tachyarrhythmia episode is detected and classified as a 1:1 tachyarrhythmia.

An arrhythmic heart rate parameter is produced at 820. The heart rate parameter represents an arrhythmic heart rate associated with the arrhythmic episode. In one embodiment, the arrhythmic heart rate parameter is produced by estimating an instantaneous heart rate associated with an arrhythmic waveform. The arrhythmic waveform is associated with an arrhythmic heart beat of the arrhythmic episode. In one embodiment, the arrhythmic heart rate parameter represents a heart rate range and is produced by mapping the estimated instantaneous heart rate to a heart rate range of a plurality of predetermined heart rate ranges.

Template feature locations of a plurality of template morphological features on a template waveform are determined using at least the heart rate parameter at 830. The template waveform is a waveform that has been produced from a cardiac signal recorded during a known cardiac rhythm, such as an NSR. A segment of the cardiac signal representing a template heart beat is digitized to be the template waveform at a sampling frequency in a range between approximately 200 and 1,000 Hz, with approximately 400 Hz being a specific example. The template waveform is divided into a plurality of template waveform segments. In one embodiment, a plurality of anchor points is located on the template waveform. The template waveform is divided into a plurality of segments using one or more anchor points of the plurality of anchor points. Examples of such anchor points include peak points, fiducial points, and turning points. In a specific embodiment, a first turning point associated with the beginning of a QRS complex and a second turning point associated with the end of the QRS complex are located. The template waveform is divided into a pre-QRS segment, a QRS segment, and a post-QRS segment using the first and second turning points. Data representative of the template waveform are stored. The data include the digitized template waveform as well as information on the anchor points and the waveform segments. In one embodiment, a template heart rate parameter representative of a template heart rate associated with the template waveform is produced and also stored. The template feature locations of the plurality of template morphological features are determined using at least the arrhythmic heart rate parameter and one or more selected anchor points of the plurality of anchor points. In one embodiment, the template feature locations are determined using one of the rate-dependent feature extraction methods illustrated in FIGS. 5A-D.

Arrhythmic feature locations of a plurality of corresponding arrhythmic morphological features on the arrhythmic waveform are determined at 840. In one embodiment, a template fiducial point is located on the template waveform, and a corresponding arrhythmic fiducial point is located on the arrhythmic waveform. Feature time intervals each between one template morphological feature of the plurality of template morphological features and the template fiducial point are measured. The arrhythmic feature locations of the plurality of corresponding arrhythmic morphological features on the arrhythmic waveform are determined using the measured time intervals and the arrhythmic fiducial point. The measured time intervals are each used as a time interval between one arrhythmic morphological feature of the plurality of corresponding arrhythmic morphological features and the arrhythmic fiducial point.

The plurality of template morphological features is extracted from the template waveform at the template feature locations at 850. The plurality of corresponding arrhythmic morphological features is extracted from an arrhythmic waveform at the arrhythmic morphological locations at 860. The plurality of template morphological features and the plurality of corresponding arrhythmic morphological features are used for the correlation analysis based on which the detected arrhythmia episode is classified.

Rate-Dependent Correlation Analysis

Figure 9:
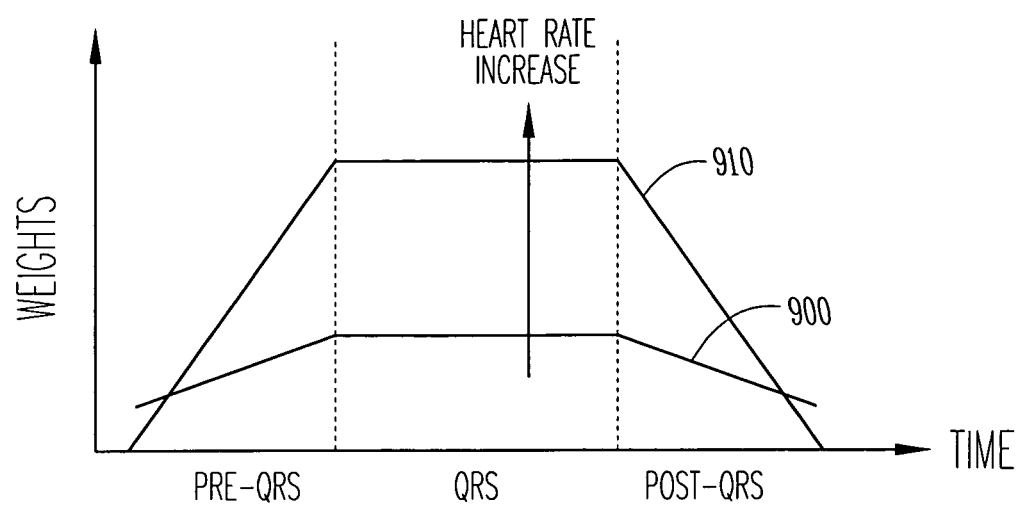
FIG. 9 is an illustration of an embodiment of a method for rate-dependent correlation analysis for discrimination of 1:1 tachyarrhythmia.

FIG. 9 is an illustration of an embodiment of rate-dependent correlation analysis for discrimination of 1:1 tachyarrhythmia. This embodiment of rate-dependent correlation analysis represents a specific embodiment of step 340 of method 300 illustrated in FIG. 3. FIG. 9 presents curves 900 and 910 each represent a set of weighting factors associated with a plurality of template morphological features and a plurality of corresponding arrhythmic morphological features. Curve 900 represents weighting factors for a relatively low heart rate, such as the template heart rate discussed above with reference to FIGS. 5A-D. Curve 910 represents weighting factors for a relatively high heart rate, such as the arrhythmic heart rate discussed above with reference to FIGS. 5A-D. The template and arrhythmic morphological features are each multiplied by a corresponding weighting factor before the correlation analysis is performed. The template waveform is divided into the pre-QRS, QRS, and post-QRS segments, as discussed above with reference to FIGS. 5A-D. As illustrated in FIG. 9, template and arrhythmic morphological features in the QRS segment are given more relative weights than the template and arrhythmic morphological features in the pre-QRS and post-QRS segments. As the heart rate increases, template and arrhythmic morphological features in the QRS segment are given even more relative weights than the template and arrhythmic morphological features in the pre-QRS and post-QRS segments. Within the pre-QRS segment, template and arrhythmic morphological features closer to the beginning of the QRS segment are given more relative weights. Within the post-QRS segment, template and arrhythmic morphological features closer to the end of the QRS segment are given more relative weights.

Figure 10:
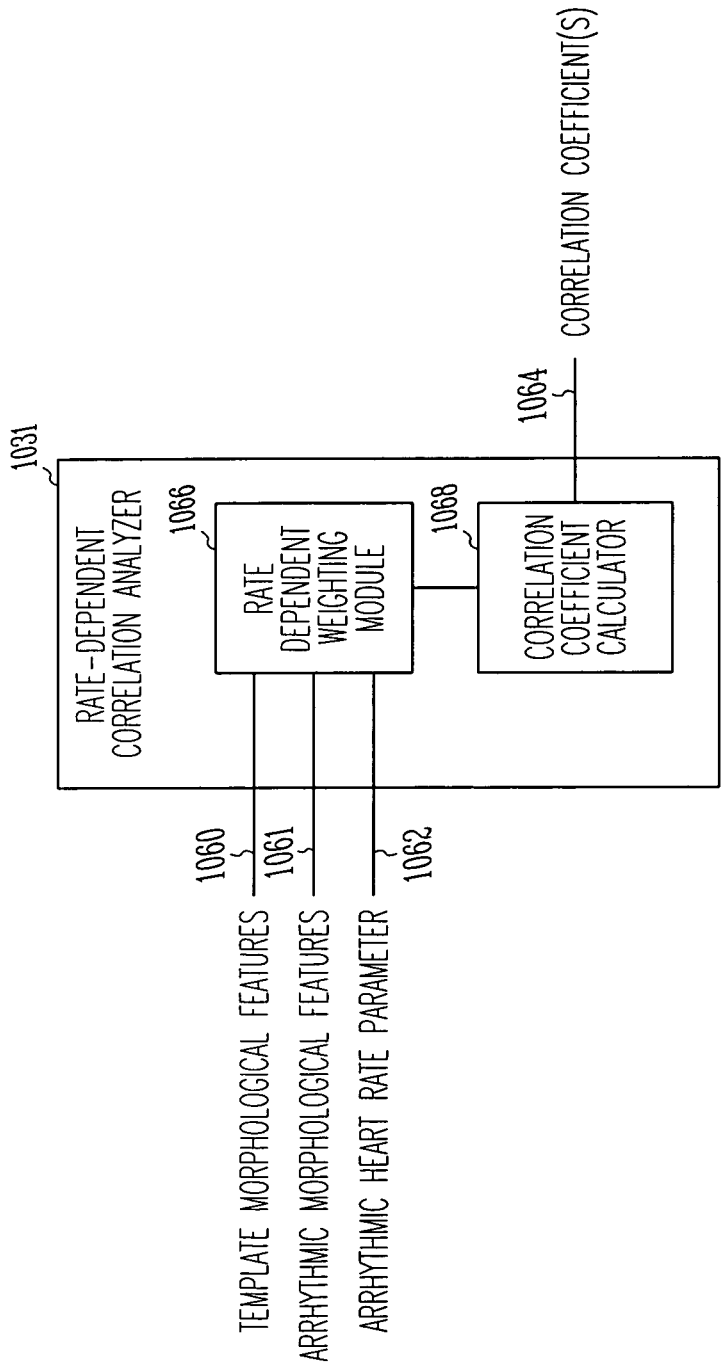
FIG. 10 is a block diagram illustrating an embodiment of a rate-dependent correlation analyzer being part of the rate-dependent morphology-based 1:1 tachyarrhythmia discrimination module.

FIG. 10 is a block diagram illustrating an embodiment of a rate-dependent correlation analyzer 1031, which is a specific embodiment of correlation analyzer 431. Rate-dependent correlation analyzer 1031 includes a template feature input 1060, an arrhythmic feature input 1061, an arrhythmic heart rate input 1062, a rate-dependent weighting module 1066, a correlation coefficient calculator 1068, and a correlation coefficient output 1064. Template feature input 1060 receives a plurality of template morphological features of a template waveform. The template waveform is associated with a template heart beat of a known cardiac rhythm, such as an NSR. Arrhythmic feature input 1061 receives a plurality of arrhythmic morphological features of an arrhythmic waveform. The arrhythmic waveform is associated with an arrhythmic heart beat of an arrhythmia episode. The arrhythmic morphological features each correspond to one of the template morphological features. Arrhythmic heart rate input 1062 receives an arrhythmic heart rate parameter representative of an arrhythmic heart rate associated with the arrhythmic waveform. Rate-dependent weighting module 1066 produces weighted template and arrhythmic morphological features by using at least the arrhythmic heart rate parameter. Correlation coefficient calculator 1068 calculates one or more correlation coefficients representative of a correlation between the weighted arrhythmic morphological features and the weighted template morphological features. Correlation coefficient output 1064 outputs the one or more correlation coefficients.

Figure 11:
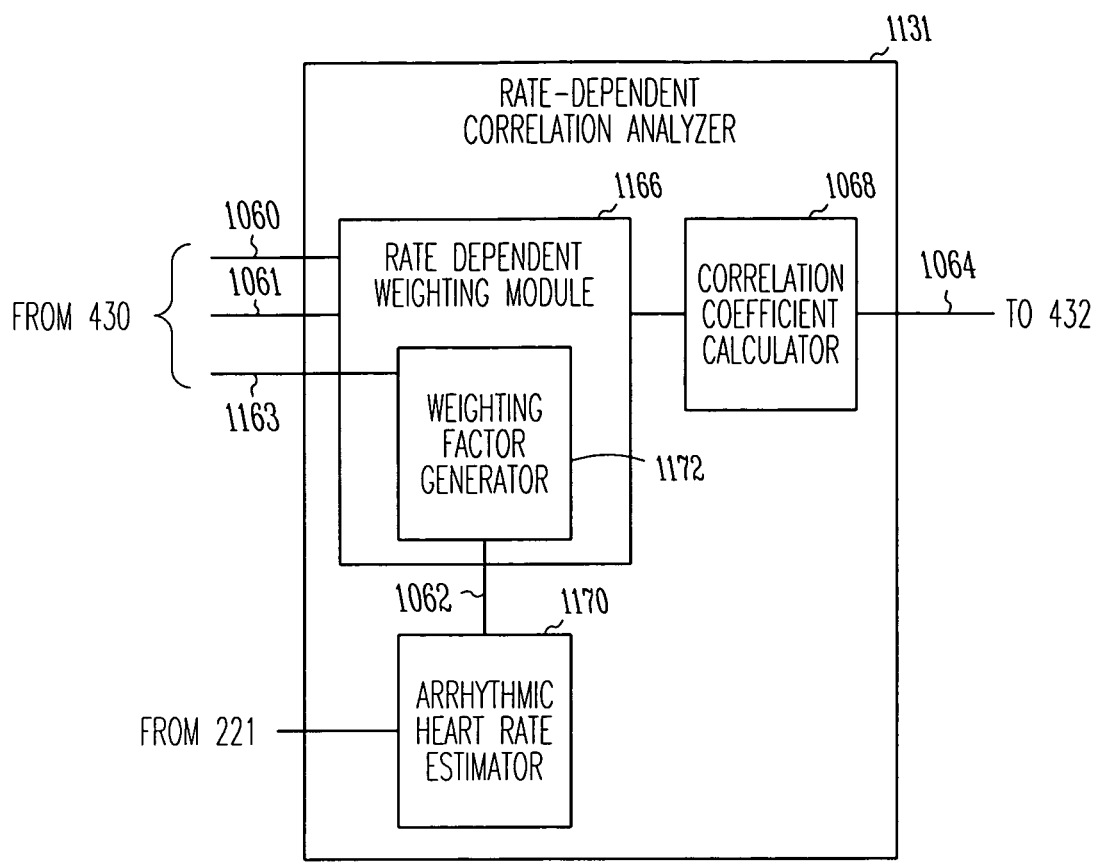
FIG. 11 is a block diagram illustrating a specific embodiment of the rate-dependent correlation analyzer of FIG. 10.

FIG. 11 is a block diagram illustrating an embodiment of a rate-dependent correlation analyzer 1131, which is a specific embodiment of rate-dependent correlation analyzer 1031. Rate-dependent correlation analyzer 1131 includes an arrhythmic heart rate estimator 1170, a rate-dependent weighting module 1166, and correlation coefficient calculator 1068. In addition, as illustrated, rate-dependent correlation analyzer 1131 includes template waveform input 1060, arrhythmic waveform input 1061, arrhythmic heart rate input 1062, correlation coefficient output 1064, and a template heart rate input 1163 that receives a template heart rate parameter representative of a template heart rate associated with the template waveform.

Arrhythmic heart rate estimator 1170 produces the arrhythmic heart rate parameter by estimating an instantaneous heart rate associated with the arrhythmic heart beat. In one embodiment, the heart rate parameter is a heart rate range that includes the estimated instantaneous heart rate. Arrhythmic heart rate estimator 1170 produce the arrhythmic heart rate parameter by estimating the instantaneous heart rate and mapping that instantaneous heart rate to one heart rate range of a plurality of predetermined heart rate ranges. This allows the weight factors to be determined by a mapping process using a reasonable number of stored weight factor value sets each corresponding to one heart rate range of the plurality of predetermined heart rate ranges. In one embodiment, the heart rate ranges each have a width of approximately 10 bpm to 50 bpm. In a specific embodiment, the heart rate ranges each have a width of approximately 20 bpm.

Rate-dependent weighting module 1166 is a specific embodiment of rate-dependent weighting module 1066 and includes a weighting factor generator 1172. Weight factor generator 1172 produces the weighting factors based on at least the arrhythmic heart rate. In one embodiment, weight factor generator 1172 produces the weighting factors based on the arrhythmic heart rate and the template heart rate. In one embodiment, weight factor generator 1172 produces the weighting factors using the method discussed above with reference to FIG. 9. Rate-dependent weighting module 1166 applies the weighting factors to the plurality of template morphological features and the plurality of corresponding arrhythmic morphological features to produce the weighted arrhythmic morphological features and the weighted template morphological features for use by correlation coefficient calculator 1068.

In one embodiment, correlation coefficient calculator 1068 calculates one or more feature correlation coefficients. One example for calculating a feature correlation coefficient is discussed in U.S. Pat. No. 6,708,058.

Figure 12:
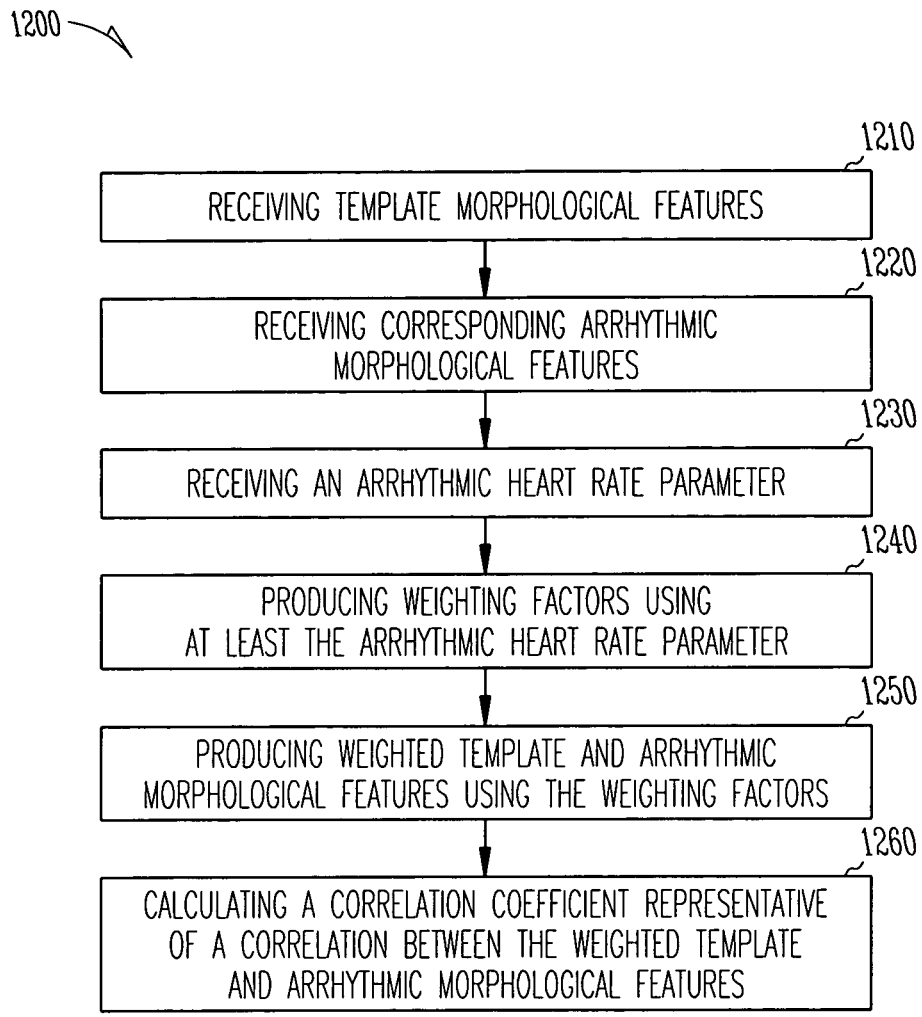
FIG. 12 is a flow chart illustrating an embodiment of a method for rate-dependent correlation analysis for discrimination of 1:1 tachyarrhythmia.

FIG. 12 is a flow chart illustrating an embodiment of a method 1200 for rate-dependent correlation analysis for discrimination of 1:1 tachyarrhythmia. In one embodiment, method 1200 is performed by tachycardia detection and classification system 120.

A plurality of template morphological features is received at 1210. The plurality of template morphological features is extracted from a template waveform. The template waveform is associated with a template heart beat of a known cardiac rhythm, such as an NSR.

A plurality of arrhythmic morphological features is received at 1220. The plurality of arrhythmic morphological features is extracted from an arrhythmic waveform. The arrhythmic waveform is associated with an arrhythmic heart beat of an arrhythmia episode. The arrhythmic morphological features each temporally correspond to one of the template morphological features.

An arrhythmic heart rate parameter is received at 1230. The arrhythmic heart rate parameter represents an arrhythmic heart rate associated with the arrhythmic waveform. In one embodiment, the arrhythmic heart rate parameter is produced by estimating an instantaneous heart rate associated with the arrhythmic waveform. In one embodiment, the arrhythmic heart rate parameter represents a heart rate range and is produced by mapping the estimated instantaneous heart rate to a heart rate range of a plurality of predetermined heart rate ranges.

Weighting factors are produced using at least the arrhythmic heart rate parameter at 1240. In one embodiment, the weighting factors are produced using the method discussed above with reference to FIG. 9.

Weighted arrhythmic morphological features and weighted template morphological features are produced using the weighting factors at 1250. A weighting factor is applied to each template morphological feature and its corresponding arrhythmic morphological feature.

A correlation coefficient representative of a correlation between the weighted template morphological features and weighted arrhythmic morphological features is calculated at 1260. In one embodiment, the correlation coefficient is a feature correlation coefficient as discussed in U.S. Pat. No. 6,708,058. The correlation coefficient is used for the classification of the arrhythmic episode.

It is to be understood that the above detailed description is intended to be illustrative, and not restrictive. For example, system 120, module 225, and their various embodiments as discussed in this document are not limited to applications in an implantable medical device, but may be incorporated into any arrhythmia analysis system, such as a computer program for analyzing pre-collected cardiac data. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for classifying cardiac arrhythmias, the system comprising:
   a tachyarrhythmia detector adapted to detect an arrhythmia episode;
   a template waveform input to receive template data representative of a template waveform associated with a template heart beat, the template waveform sensed during a normal sinus rhythm;
   an arrhythmic waveform input to receive arrhythmic data representative of an arrhythmic waveform associated with an arrhythmic heart beat sensed during the detected arrhythmia episode;
   an arrhythmic heart rate input to receive an arrhythmic heart rate parameter representative of an arrhythmic heart rate associated with the detected arrhythmic episode;
   a rate-dependent feature locator coupled to the template waveform input, the arrhythmic waveform input, and the arrhythmic heart rate parameter input, the rate-dependent feature locator adapted to dynamically determine morphological feature locations each as a function of at least the arrhythmic heart rate parameter in response to the detected arrhythmia episode, the morphological feature locations including template feature locations each representative of timing of a plurality of template morphological features on the template waveform and arrhythmic feature locations each representative of timing of a plurality of corresponding arrhythmic morphological features on the arrhythmic waveform; and
   a feature extracting module coupled to the rate-dependent feature locator, the feature extracting module adapted to extract the plurality of template morphological features from the template waveform at the dynamically determined morphological feature locations and to extract the plurality of corresponding arrhythmic morphological features from the arrhythmic waveform at the dynamically determined morphological feature locations.

2. The system of claim 1, further comprising:
   a correlation analyzer, coupled to the feature extracting module, to produce at least one correlation coefficient representative of a correlation between the plurality of template morphological features and the plurality of corresponding arrhythmic morphological features; and
   an arrhythmia classification module, coupled to the correlation analyzer, to classify the detected arrhythmia episode based on the at least one correlation coefficient.

3. The system of claim 1, further comprising an arrhythmic heart rate estimator coupled to the arrhythmic heart rate input, the arrhythmic heart rate estimator adapted to produce the arrhythmic heart rate parameter by estimating an instantaneous heart rate associated with the arrhythmic heart beat.

4. The system of claim 3, wherein the arrhythmic heart rate estimator is further adapted to produce the arrhythmic heart rate parameter by mapping the estimated instantaneous heart rate to one heart rate range of a plurality of predetermined heart rate ranges.

5. The system of claim 1, further comprising a template heart rate input to receive the template heart rate parameter representative of a template heart rate associated with the template waveform, and wherein the rate-dependent feature locator is further coupled to the template heart rate parameter input and adapted to determine the morphological feature locations using at least the arrhythmic heart rate parameter and the template heart rate parameter.

6. The system of claim 5, further comprising:
   a template waveform storage device, coupled to the template waveform input, to store the template data including a digitized template waveform having approximately 64 to 320 sample points; and
   a template generator, coupled to the template waveform storage device, to produce the digitized template waveform by sampling a cardiac signal at a sampling frequency in a range of approximately 200 to 1,000 Hz.

7. The system of claim 5, further comprising:
   a template waveform storage device, coupled to the template waveform input, to store the template data;
   a template generator, coupled to the template waveform storage device, to produce the template data;
   an anchor point locator coupled to the template generator, the anchor point locator adapted to locate a plurality of anchor points on the template waveform; and
   a waveform divider coupled to the template generator, the anchor point locator, and the template waveform storage device, the waveform divider adapted to divide the template waveform into a plurality of template waveform segments using one or more anchor points of the plurality of anchor points.

8. The system of claim 7, wherein the rate-dependent feature locator comprises a template feature locator adapted to determine the template feature locations using the arrhythmic heart rate parameter, the template heart rate parameter, and one or more selected anchor points of the plurality of anchor points.

9. The system of claim 8, wherein the rate-dependent feature locator comprises:
   a fiducial point locator adapted to locate a template fiducial point on the template waveform and a corresponding arrhythmic fiducial point on the arrhythmic waveform;
   a feature timing module to measure feature time intervals each between one template morphological feature of the plurality of template morphological features and the template fiducial point; and
   an arrhythmic feature locator adapted to determine the arrhythmic feature locations on the arrhythmic waveform using the measured time intervals each as a time interval between one arrhythmic morphological feature of the plurality of corresponding arrhythmic morphological features and the arrhythmic fiducial point.

10. The system of claim 7, wherein the anchor point locator comprises a turning point locator to locate a first turning point associated with a start of a QRS complex and a second turning point associated with an end of the QRS complex, and the waveform divider is adapted to divide the template waveform into a pre-QRS segment, a QRS segment, and a post-QRS segment using the first and second turning points.

11. The system of claim 10, wherein the rate-dependent feature locator comprises a template feature locator adapted to select the first and second turning points as two of the template feature locations.

12. The system of claim 11, wherein the template feature locator is adapted to select one or more pre-QRS template feature locations each having a first timing relationship with the first turning point from the pre-QRS segment and one or more post-QRS template feature locations each having a second timing relationship with the second turning point from the post-QRS segment, the first timing relationship being a first function of the arrhythmic heart rate parameter, the second timing relationship being a second function of the arrhythmic heart rate parameter.

13. The system of claim 11, wherein the template feature locator is adapted to select a plurality of QRS template feature locations from the QRS segment, the selected QRS template feature locations being a function of the arrhythmic heart rate parameter.

14. A method for classifying cardiac arrhythmias using an implantable medical device, the method comprising:
  detecting an arrhythmia episode;
  producing a heart rate parameter representative of an arrhythmic heart rate associated with the detected arrhythmia episode;
  dynamically determining morphological feature locations each as a function of at least the heart rate parameter in response to the detected arrhythmia episode, the morphological feature locations including template feature locations each representative of timing of a plurality of template morphological features on a template waveform associated with a template heart beat and arrhythmic feature locations each representative of timing of a plurality of corresponding arrhythmic morphological features on an arrhythmic waveform associated with an arrhythmic heart beat, the template waveform sensed by the implantable medical device during a normal sinus rhythm and stored in the implantable medical device, the arrhythmic waveform sensed by the implantable medical device during the detected arrhythmia episode;
  extracting the plurality of template morphological features from the template waveform at the dynamically determined morphological feature locations; and
  extracting the plurality of corresponding arrhythmic morphological features from the arrhythmic waveform at the dynamically determined morphological feature locations.

15. The method of claim 14, wherein producing the heart rate parameter comprises:
  estimating an instantaneous heart rate associated with the arrhythmic waveform; and
  mapping the estimated instantaneous heart rate to a heart rate range of a plurality of predetermined heart rate ranges.

16. The method of claim 14, further comprising:
  producing template data representative of the template waveform; and
  storing the template data,
  wherein producing the template data comprises locating a plurality of anchor points on the template waveform and dividing the template waveform into a plurality of template waveform segments using one or more anchor points of the plurality of anchor points.

17. The method of claim 16, wherein determining the morphological feature locations comprises:
  selecting one or more locations of the anchor points as one or more locations of the template feature locations; and
  selecting a plurality of additional locations of the template feature locations based on timing relationships each between one of the additional locations and one of the one or more locations of the anchor points, the timing relationships each being a function of the arrhythmic heart rate parameter.

18. The method of claim 17, wherein determining the morphological feature locations comprises:
  locating a template fiducial point on the template waveform and a corresponding arrhythmic fiducial point on the arrhythmic waveform;
  measuring feature time intervals each between one template morphological feature of the plurality of template morphological features and the template fiducial point; and
  determining the arrhythmic feature locations of the plurality of corresponding arrhythmic morphological features on the arrhythmic waveform using the arrhythmic fiducial point and the measured feature time intervals.

19. The method of claim 16, wherein locating the plurality of anchor points comprises locating a first turning point associated with a start of a QRS complex and a second turning point associated with an end of the QRS complex, and dividing the template waveform into a plurality of template waveform segments comprises dividing the template waveform into a pre-QRS segment, a QRS segment, and a post-QRS segment using the first and second turning points.

20. The method of claim 19, wherein determining the morphological feature locations comprises:
  selecting the first and second turning points as two of the template feature locations;
  selecting one or more pre-QRS template feature locations each having a first timing relationship with the first turning point from the pre-QRS segment, the first timing relationship being a first function of the arrhythmic heart rate parameter; and
  selecting one or more post-QRS template feature locations each having a second timing relationship with the second turning point from the post-QRS segment, the second timing relationship being a second function of the arrhythmic heart rate parameter.

21. The method of claim 19, wherein determining the morphological feature locations comprises:
  selecting the first and second turning points as two of the template feature locations; and
  selecting a plurality of QRS template feature locations from the QRS segment, the selected QRS template feature locations being a function of the arrhythmic heart rate parameter.

22. The method of claim 21, wherein selecting the plurality of QRS template feature locations comprises determining a quantity of the QRS template feature locations based on the arrhythmic heart rate parameter.

23. A system for classifying cardiac arrhythmias, the system comprising:
  a tachyarrhythmia detector adapted to detect an arrhythmia episode;
  a template feature input to receive a plurality of template morphological features of a template waveform associated with a template heart beat of a known cardiac rhythm;
  an arrhythmic feature input to receive a plurality of arrhythmic morphological features of an arrhythmic waveform associated with an arrhythmic heart beat of the detected arrhythmia episode, the arrhythmic morphological features each corresponding to one of the template morphological features;
  an arrhythmic heart rate input to receive an arrhythmic heart rate parameter representative of an arrhythmic heart rate associated with the arrhythmic waveform;
  a rate-dependent weighting module coupled to the template feature input, the arrhythmic feature input, and the arrhythmic heart rate input and including a weighting factor generator adapted to produce weighting factors each as a function of at least the arrhythmic heart rate parameter, the rate-dependent weighting module adapted to produce weighted template morphological features and weighted arrhythmic morphological features by applying one of the weighting factors to each template morphological feature of the plurality of template morphological features and each arrhythmic morphological feature of the plurality of arrhythmic morphological features in response to the detected arrhythmia episode; and a correlation coefficient calculator, coupled to the rate-dependent weighting module, to calculate at least one correlation coefficient representative of a correlation between the weighted arrhythmic morphological features and the weighted template morphological features.

24. The system of claim 23, further comprising an arrhythmia classification module, coupled to the correlation coefficient calculator, to classify the detected arrhythmia episode based on the at least one correlation coefficient.

25. The system of claim 23, further comprising a template heart rate input, coupled to the rate-dependent weighting module, to receive a template heart rate parameter representative of a template heart rate associated with the template waveform, and wherein the weighting factor generator is adapted to produce weighting factors each as a function of at least the arrhythmic heart rate parameter and the template heart rate parameter.

26. The system of claim 23, further comprising an arrhythmic heart rate estimator coupled to the arrhythmic heart rate input, the arrhythmic heart rate estimator adapted to produce the arrhythmic heart rate parameter by estimating an instantaneous heart rate associated with the arrhythmic heart beat.

27. The system of claim 26, wherein the arrhythmic heart rate estimator is further adapted to produce the arrhythmic heart rate parameter by mapping the estimated instantaneous heart rate to one heart rate range of a plurality of predetermined heart rate ranges.

28. The system of claim 27, wherein the weighting factor generator is adapted to map the arrhythmic heart rate parameter to one set of weight factors of a plurality of sets of predetermined weighting factors.

29. A method for classifying cardiac arrhythmias using an implantable medical device, the method comprising:
  detecting an arrhythmia episode;
  receiving a plurality of template morphological features of a template waveform associated with a template heart beat of a known cardiac rhythm, the template waveform sensed by the implantable medical device during the known cardiac rhythm and stored in the implantable medical device;
  receiving a plurality of arrhythmic morphological features of an arrhythmic waveform associated with an arrhythmic heart beat of the detected arrhythmia episode, the arrhythmic morphological features each corresponding to one of the template morphological features, the arrhythmic waveform sensed by the implantable medical device during the detected arrhythmia episode;
  receiving an arrhythmic heart rate parameter representative of an arrhythmic heart rate associated with the arrhythmic waveform;
  producing a plurality of weighting factors each as a function of at least the arrhythmic heart rate parameter;
  producing weighted template morphological features and weighted arrhythmic morphological features by applying a weighting factor of the plurality of weighting factors to each of the template morphological features and each of the arrhythmic morphological features in response to the detected arrhythmia episode;
  analyzing a correlation between the weighted template morphological features and the weighted arrhythmic morphological features; and
  classifying the detected arrhythmia episode based on the correlation.

30. The method of claim 29, further comprising receiving a template heart rate parameter representative of a template heart rate associated with the template waveform, and wherein producing the plurality of weighting factors comprises producing the plurality of weighting factors using at least the arrhythmic heart rate parameter and the template heart rate parameter.

31. The method of claim 30, further comprising producing the arrhythmic heart rate parameter by estimating an instantaneous heart rate associated with the arrhythmic heart beat.

32. The method of claim 31, wherein producing the plurality of weighting factors comprises:
  mapping the estimated instantaneous heart rate to one heart rate range of a plurality of predetermined heart rate ranges; and
  mapping the heart rate range to one set of weight factors of a plurality of sets of predetermined weighting factors.

33. The method of claim 29, wherein producing the plurality of weighting factors comprises producing weighting factors to allow a relative weight of each of template QRS morphological features to increase with the arrhythmic heart rate, the template QRS morphological features each being one of the plurality of template morphology features extracted from a QRS complex of the template waveform.

34. The method of claim 33, wherein producing the plurality of weighting factors comprises producing weighting factors giving the template QRS morphological features relatively high weights and giving remaining template morphological features of the plurality of template morphological features relatively low weights.

* * * * *